(12) United States Patent
Pawlak et al.

(10) Patent No.: US 7,687,669 B2
(45) Date of Patent: Mar. 30, 2010

(54) METHOD FOR DIRECT-OXYGENATION OF ALKANE GASES

(75) Inventors: Nathan A. Pawlak, Charlevoix, MI (US); Robert W. Carr, Bloomington, MN (US); Roger J. Grunch, Charlevoix, MI (US)

(73) Assignee: Gas Technologies LLC, Walloon Lake, MI (US)

( * ) Notice: Subject to any disclaimer, the term of this patent is extended or adjusted under 35 U.S.C. 154(b) by 0 days.

(21) Appl. No.: 12/273,213

(22) Filed: Nov. 18, 2008

(65) Prior Publication Data

US 2009/0118553 A1 May 7, 2009

Related U.S. Application Data

(60) Division of application No. 11/685,867, filed on Mar. 14, 2007, now Pat. No. 7,456,327, which is a continuation-in-part of application No. PCT/US2007/004557, filed on Feb. 19, 2007, and a continuation-in-part of application No. PCT/US2007/004297, filed on Feb. 19, 2007, and a continuation-in-part of application No. PCT/US2007/004185, filed on Feb. 19, 2007, each which is a continuation-in-part of application No. 11/526,824, filed on Sep. 25, 2006, and a continuation-in-part of application No. 11/446,371, filed on Jun. 2, 2006, now abandoned, and a continuation-in-part of application No. 11/432,692, filed on May 11, 2006, and a continuation-in-part of application No. 11/351,532, filed on Feb. 10, 2006, each which is a continuation-in-part of application No. 11/319,093, filed on Dec. 27, 2005.

(51) Int. Cl.
C07C 41/02 (2006.01)
C07C 27/10 (2006.01)

(52) U.S. Cl. .................. 568/910.5; 568/910

(58) Field of Classification Search .............. 568/910, 568/910.5
See application file for complete search history.

(56) References Cited

U.S. PATENT DOCUMENTS

| | | | |
|---|---|---|---|
| 1,038,547 A | 9/1912 | Fernekes |
| 1,500,080 A | 7/1924 | Kloppenburg |
| 1,776,771 A | 9/1930 | Boomer |
| 2,196,188 A | 4/1940 | Bone et al. |
| 2,244,241 A | 6/1941 | Bryce |
| 2,384,028 A | 9/1945 | Hall |
| 2,467,993 A | 4/1949 | Rossman |
| 2,722,553 A | 11/1955 | Mullen |
| 2,922,809 A | 1/1960 | Oberdorfer, Jr. |
| 3,027,411 A | 3/1962 | Murphy |
| 3,130,026 A | 4/1964 | Becker |
| 3,145,220 A | 8/1964 | Bartok |
| 3,232,991 A | 2/1966 | Magee |
| 3,483,229 A | 12/1969 | Bernard |
| 3,689,575 A | 9/1972 | Tarhan |
| 3,718,006 A | 2/1973 | Ranke |
| 3,920,717 A | 11/1975 | Marion |
| 3,940,428 A | 2/1976 | Connell et al. |
| 3,975,172 A | 8/1976 | Ranke |
| 3,977,203 A | 8/1976 | Hinton et al. |
| 3,993,457 A | 11/1976 | Cahn et al. |
| 4,067,972 A | 1/1978 | Oswald et al. |
| 4,144,314 A | 3/1979 | Doerges et al. |
| 4,149,940 A | 4/1979 | Pinto |
| 4,152,407 A | 5/1979 | Fuchs |
| 4,203,915 A | 5/1980 | Supp et al. |
| 4,243,457 A | 1/1981 | Mayumi et al. |
| 4,243,613 A | 1/1981 | Brockhaus et al. |
| 4,252,548 A | 2/1981 | Markbreiter et al. |
| 4,271,086 A | 6/1981 | Supp et al. |
| 4,289,709 A | 9/1981 | Kaiser |
| 4,289,710 A | 9/1981 | Kaiser |

(Continued)

FOREIGN PATENT DOCUMENTS

EP 0 790 226 12/1996

(Continued)

OTHER PUBLICATIONS

Marafee, A. et al., "An Experimental Study on the Oxidative Coupling of Methane in a Direct Current Corona Discharge Reactor over Sr/La2O3 Catalyst", Industrial & Engineering Chemistry Research, vol. 36, No. 3, 1997, pp. 632-637.

(Continued)

Primary Examiner—Jafar Parsa
(74) Attorney, Agent, or Firm—Brooks Kushman P.C.

(57) ABSTRACT

A method for alkyl oxygenate (e.g., methanol) manufacture via partial oxidation of alkane (methane) uses an injectively-mixed backmixing reaction chamber in fluid communication with a tubular-flow reactor. Alkyl free radicals are induced in the backmixing reaction chamber prior to being fed through a flow-restriction baffle to the tubular-flow reactor. Injective intermixing of feed streams agitates the backmixing reaction chamber. In one embodiment, a variable position flow restriction baffle is axially moved to commensurately modify the backmixing reaction chamber and tubular-flow reactor volumes. In another embodiment, the tubular-flow reactor is quenched with a variable position quenching input. The method further provides for condensing the output stream from the reaction system in a condensing scrubber and also for recycling a portion of the scrubbed output stream to the reactor system.

3 Claims, 21 Drawing Sheets

U.S. PATENT DOCUMENTS

| | | |
|---|---|---|
| 4,311,671 A | 1/1982 | Notman |
| 4,312,955 A | 1/1982 | Bartley |
| 4,324,567 A | 4/1982 | Ranke et al. |
| 4,346,179 A | 8/1982 | Sugier et al. |
| 4,353,712 A | 10/1982 | Marion et al. |
| 4,366,260 A | 12/1982 | Wainwright et al. |
| 4,374,288 A | 2/1983 | Scragg |
| 4,386,941 A | 6/1983 | Crouch et al. |
| 4,392,869 A | 7/1983 | Marion et al. |
| 4,394,137 A | 7/1983 | Marion et al. |
| 4,400,180 A | 8/1983 | Marion et al. |
| 4,430,316 A | 2/1984 | Ranke et al. |
| 4,443,560 A | 4/1984 | LeBlanc, Jr. et al. |
| 4,476,250 A | 10/1984 | Joyner et al. |
| 4,479,810 A | 10/1984 | Marion et al. |
| 4,490,156 A | 12/1984 | Marion et al. |
| 4,530,826 A | 7/1985 | Ohashi |
| 4,540,712 A | 9/1985 | Dombek |
| 4,564,643 A | 1/1986 | Shibata et al. |
| 4,575,387 A | 3/1986 | Larne et al. |
| 4,606,741 A | 8/1986 | Moreau et al. |
| 4,608,447 A | 8/1986 | Mazanec et al. |
| 4,609,388 A | 9/1986 | Adler et al. |
| 4,614,749 A | 9/1986 | Sapienza et al. |
| 4,618,732 A | 10/1986 | Gesser et al. |
| 4,619,946 A | 10/1986 | Sapienza et al. |
| 4,623,668 A | 11/1986 | Broecker et al. |
| 4,628,065 A | 12/1986 | Prouteau et al. |
| 4,628,066 A | 12/1986 | Bonnell et al. |
| 4,670,473 A | 6/1987 | Walker et al. |
| 4,721,458 A | 1/1988 | Conrad |
| 4,747,858 A | 5/1988 | Gottier |
| 4,760,210 A | 7/1988 | Sweeney |
| 4,782,096 A | 11/1988 | Banquy |
| 4,816,121 A | 3/1989 | Keefer |
| 4,822,393 A | 4/1989 | Markbreiter et al. |
| 4,861,360 A | 8/1989 | Apffel |
| 4,868,221 A | 9/1989 | Sie et al. |
| 4,873,267 A | 10/1989 | Sie et al. |
| 4,888,361 A | 12/1989 | Sie et al. |
| 4,982,023 A | 1/1991 | Han et al. |
| 5,012,029 A | 4/1991 | Han et al. |
| 5,015,798 A | 5/1991 | Han et al. |
| 5,063,250 A | 11/1991 | Murayama et al. |
| 5,067,972 A | 11/1991 | Hemmings et al. |
| 5,132,472 A | 7/1992 | Durante et al. |
| 5,177,279 A | 1/1993 | Harandi |
| 5,180,570 A | 1/1993 | Lee et al. |
| 5,220,080 A | 6/1993 | Lyons et al. |
| 5,384,335 A | 1/1995 | Tierney et al. |
| 5,496,859 A | 3/1996 | Fong et al. |
| 5,631,302 A | 5/1997 | Konig et al. |
| 5,735,936 A | 4/1998 | Minkkinen et al. |
| 5,770,630 A | 6/1998 | Kowal et al. |
| 5,861,441 A | 1/1999 | Waycuilis |
| 5,883,138 A | 3/1999 | Hershkowitz et al. |
| 5,886,056 A | 3/1999 | Hershkowitz et al. |
| 5,959,168 A | 9/1999 | Aalast |
| 6,028,119 A | 2/2000 | Kokubu et al. |
| 6,102,987 A | 8/2000 | Gross et al. |
| 6,139,605 A | 10/2000 | Carnell et al. |
| 6,153,149 A | 11/2000 | Rabitz et al. |
| 6,159,432 A | 12/2000 | Mallinson et al. |
| 6,267,912 B1 | 7/2001 | Hershkowitz et al. |
| 6,300,380 B1 | 10/2001 | Kobayashi et al. |
| 6,328,854 B1 | 12/2001 | Sherman et al. |
| 6,342,091 B1 | 1/2002 | Menzel et al. |
| 6,447,745 B1 | 9/2002 | Feeley et al. |
| 6,595,291 B1 | 7/2003 | Lia et al. |
| 6,625,988 B2 | 9/2003 | Weisenstein et al. |
| 6,632,971 B2 | 10/2003 | Brown et al. |
| 6,645,272 B2 | 11/2003 | Lemaire et al. |
| 6,667,347 B2 | 12/2003 | O'Rear et al. |
| 6,720,359 B2 | 4/2004 | O'Rear et al. |
| 6,726,850 B1 | 4/2004 | Reyes et al. |
| 6,736,955 B2 | 5/2004 | Shaw |
| 6,881,389 B2 | 4/2005 | Paulsen et al. |
| 6,881,758 B2 | 4/2005 | Guillard et al. |
| 6,942,719 B2 | 9/2005 | Stewart |
| 7,028,478 B2 | 4/2006 | Prentice, III |
| 7,067,558 B2 | 6/2006 | Grobys et al. |
| 7,071,238 B2 | 7/2006 | Gamlin et al. |
| 7,083,662 B2 | 8/2006 | Xu et al. |
| 7,108,838 B2 | 9/2006 | McGee |
| 2001/0006615 A1 | 7/2001 | Badano |
| 2002/0177741 A1 | 11/2002 | Allison et al. |
| 2003/0032844 A1 | 2/2003 | Seiki et al. |
| 2003/0065042 A1 | 4/2003 | Shaw |
| 2004/0065199 A1 | 4/2004 | Rojey et al. |
| 2004/0123523 A1 | 7/2004 | Rong et al. |
| 2004/0171701 A1 | 9/2004 | Shaw |
| 2006/0035986 A1 | 2/2006 | Bichkov et al. |
| 2006/0235088 A1 | 10/2006 | Olah et al. |
| 2006/0264683 A1 | 11/2006 | Knox et al. |

FOREIGN PATENT DOCUMENTS

| | | |
|---|---|---|
| GB | 2 159 153 A | 11/1985 |
| GB | 2196335 | 4/1988 |
| JP | 63001438 | 1/1988 |
| JP | 2004 315413 | 11/2004 |
| RU | 2 162 460 | 1/2001 |
| RU | 2 203 261 | 4/2002 |
| RU | 2 200 731 | 3/2003 |
| SU | 1 336 471 | 9/1996 |
| SU | 1 469 788 | 11/1996 |
| WO | 96 06901 | 3/1996 |
| WO | 03 031380 | 4/2003 |

OTHER PUBLICATIONS

Burch, et al., "Direct Conversion of Methane into Methanol", J. Chem. Soc., Faraday Trans. 1, 1989, 85(10), pp. 3561-3568.

Liu, C. et al., "Comparative Investigations on Plasma Catalytic Methane Conversion to Higher Hydrocarbons over Zeolites", Applied Catalysis A: General 178, 1999, pp. 17-27.

Liu, C. et al., "Experimental Investigations on the Interaction Between Plasmas and Catalyst for Plasma Catalytic Methane Conversion (PCMC) over Zeolites", Natural Gas Conversion V, Studies in Surface Science and Catalysis, col. 119, 1998, pp. 361-366.

Liu, C. et al., "Methane Conversion to Higher Hydrocarbons in a Corona Discharge Over Metal Oxide Catalysts with OH Groups", 1997, Applied Catalysis A: General 164, pp. 21-33.

Liu, C. et al., "Modification of NaY Zeolite in a Corona Discharge and its Application for the Reduction of Carbon Dioxide", Greenhouse Gas Control Technologies, 1999, pp. 1103-1105.

Liu, C. et al., "Nonoxidative Methane Conversion to Acetylene over Zeolite in a Low Temperature Plasma", Journal of Catalysis 179, 1998, pp. 326-334.

Liu, C. et al., "Oxidative Coupling of Methane with AC and DC Corona Discharges", Industrial & Engineering Chemistry Research, vol. 35, No. 10, 1996, pp. 3295-3301.

Gordon, C.L. et al., "Selective Hydrogenation of Acetylene to Ethylene During the Conversion of Methane in a Catalytic DC Plasma Reactor", Studies in Surface Science and Catalysis, vol. 36: Natural Gas Conversion VI, 2001, pp. 271-276.

Gordon, C.L. et al., "The Production of Hydrogen From Methane Using Tubular Plasma Reactors", Advances in Hydrogen Energy, 2000, pp. 57-67.

Koert, D.N. et al., A flow reactor for the study of homogeneous gas-phase oxidation of hydrocarbons at pressure up to 20 atm (2MPa), Mar. 1992, 7 pgs.

Larkin, D.W. et al., "Carbon Pathways, Co2 Utilization, and In Situ Product Removal in Low Temperature Plasma Methane Conversion to Methanol", Greenhouse Gas Control Technologies, 1999, pp. 397-402.

Larkin, D.W. et al., "Oxygen Pathways and Carbon Dioxide Utilization in Methane Partial Oxidation in Ambient Temperature Electric Discharges", Energy & Fuels 1998, 12, pp. 740-744.

Larkin, D.W. et al., "Product Selectivity Control and Organic Oxygenate Pathways From Partial Oxidation of Methane in a Silent Electric Discharge Reactor", Ind. Eng. Chem. Res. 2001, 40, pp. 5496-5506.

Larkin, D.W. et al., "Production of Organic Oxygenates in the Partial Oxidation of Methane in a Silent Electric Discharge Reactor", Ind. Eng. Chem. Res. 2001, 40, pp. 1594-1601.

Ranzi, E. et al., "A New Comprehensive Reaction Mechanism for Combustion of Hydrocarbon Fuels", Prepared for the Twenty-Fifth International Symposium on Combustion Jul. 31-Aug. 5, 1994, Dec. 3, 1993, 23 pgs.

Sheverdenkin, E.V. et al., "Kinetics of Partial Oxidation of Alkanes at High Pressures; Oxidation of Ethane and Methane-Ethane Mixtures", Theoretical Foundations of Chemical Engineering, vol. 38, No. 3, 2004, pp. 311-315.

Foulds, G. et al., "Kinetics, Catalysis, and Reaction Engineering—Homogeneous Gas-Phase Oxidation of Methane Using Oxygen as Oxidant in an Annular Reactor", Ind. Eng. Chem. Res. 1993, 32, pp. 780-787.

Henni, et al., "Solubility of Carbon Dioxide in Methyldiethanolamine + Methanol + Water", Journal of Chemical Engineering Data, 1995, 40, pp. 493-495.

Supat, K. et al., "Combined Steam Reforming and Partial Oxidation of Methane to Synthesis Gas Under Electrical Discharge", Ind. Engr. Chem. Res., 2003, 42, Page Est: 7.2 (A-H).

Supat, K. et al., "Synthesis Gas Production From Partial Oxidation of Methane with Air in AC Electric Gas Discharge", Energy & Fuels, 2003, 17, pp. 474-481.

Thanyachotpaiboon, K. et al., "Conversion of Methane to Higher Hydrocarbons in AC Nonequilibrium Plasmas", AIChE Journal, Oct. 1998, vol. 4, No. 10, pp. 2252-2257.

Lodeng, et al., "Experimental and Modeling Study of the Selective Homogeneous Gas Phase Oxidation of Methane to Methanol", Industrial Engineering Chemical Res., 1995, pp. 1044-1059.

Karaveav, M.M. et al., "Technology of Synthetic Methanol", Moscow, Chemistry, 1984 pp. 72-125.

Bhatnagar, R. et al., "Methane Conversion in AC Electric Discharges at Ambient Conditions", Plenum Publishing, NY 1995 pp. 249-264.

Caldwell, T.A. et al., "Partial Oxidation of Methane to Form Synthesis Gas in a Tubular AC Plasma Reactor", Studies in Surface Science and Catalysis, vol. 36: Natural Gas Conversion VI, 2001, pp. 265-270.

Arutyunov, V., "Recent Results on Fast Flow Gas-Phase Partial Oxidation of Lower Alkanes", Journal of Natural Gas Chemistry 13 (2004), 13 pgs.

Zang, et al., "Recent Progress in Direct Partial Oxidation of Methane to Methanol", Journal of Natural Gas Chemistry, vol. 12, No. 2, 2003, pp. 81-89.

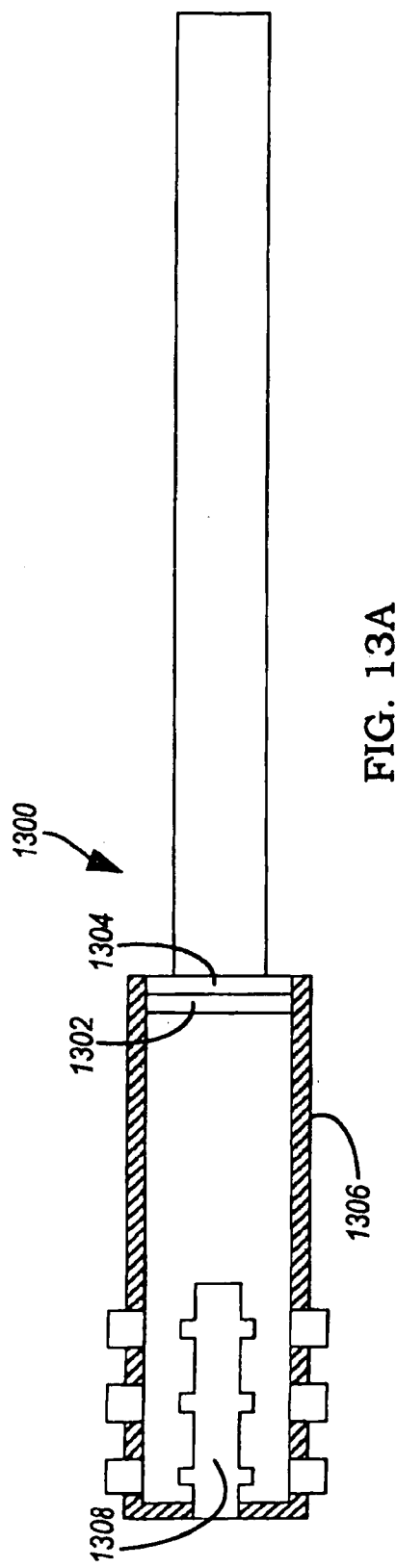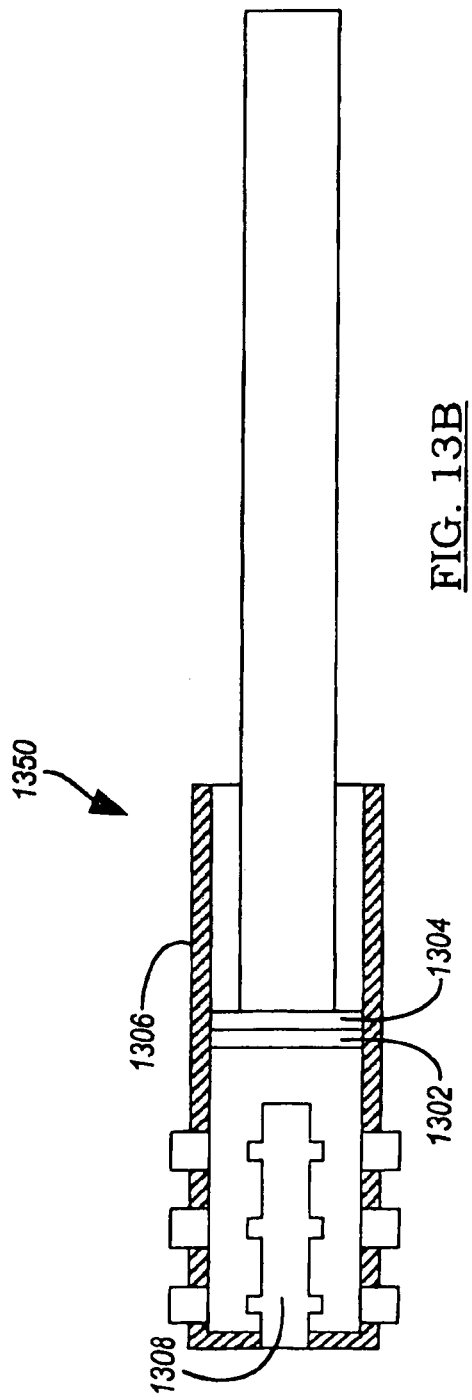

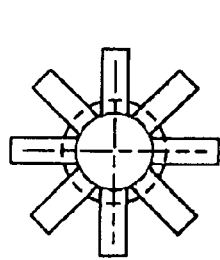
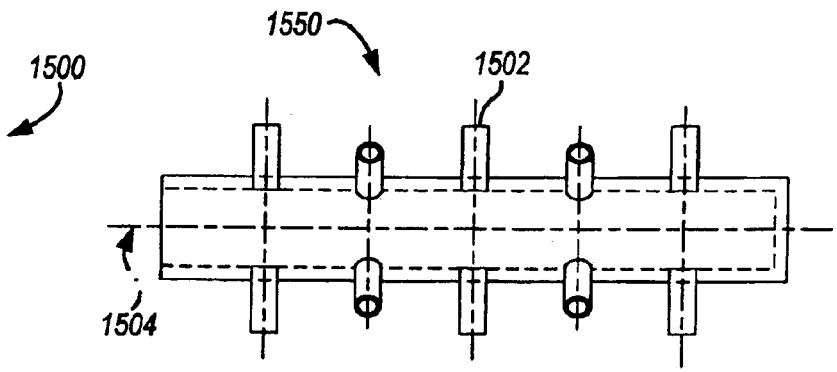
FIG. 15A
FIG. 15B
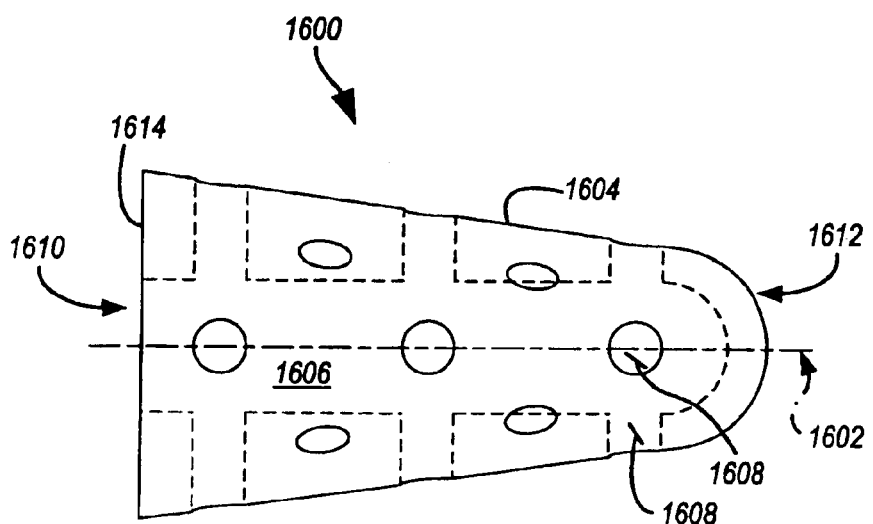
FIG. 16

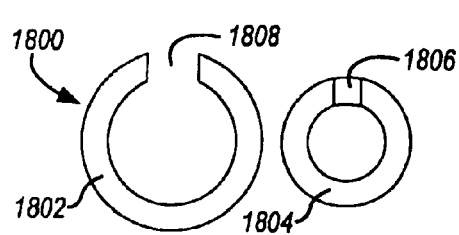
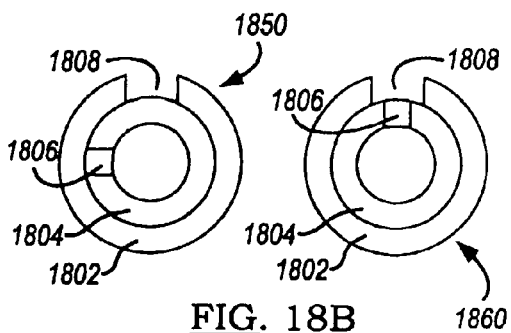
FIG. 18A  FIG. 18B
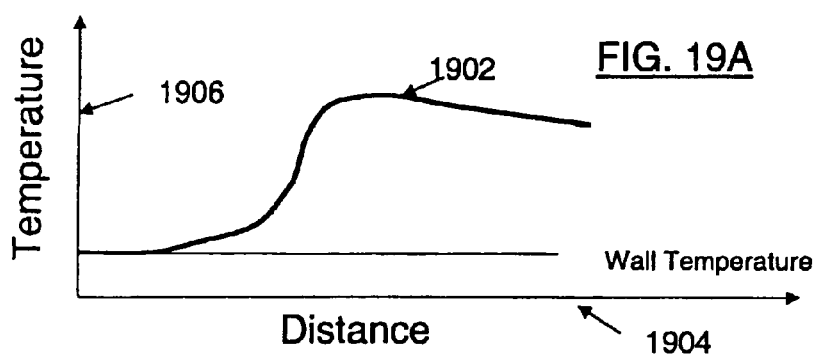
FIG. 19A
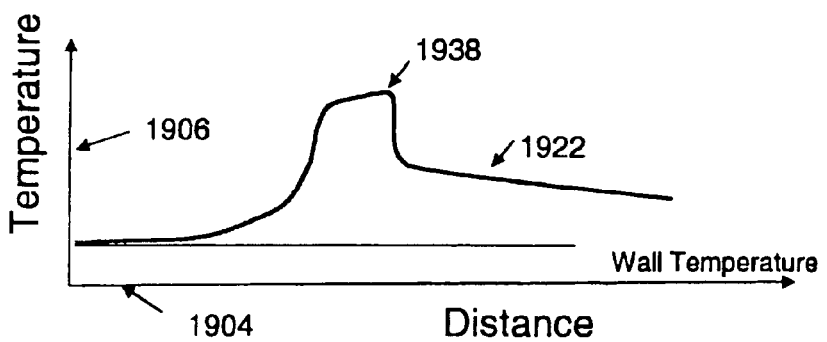
FIG. 19B

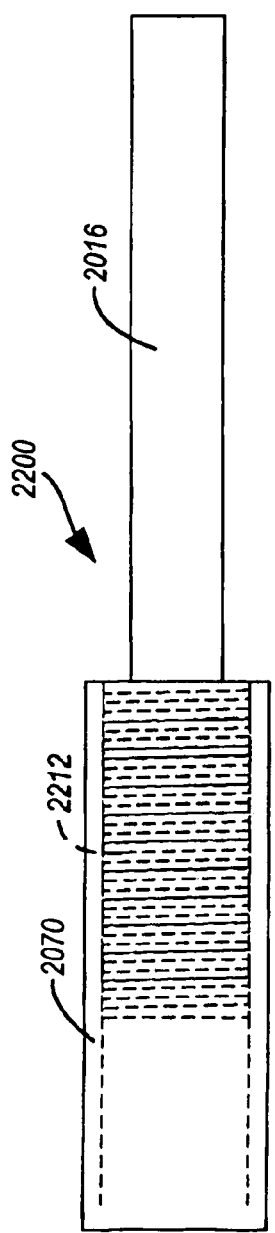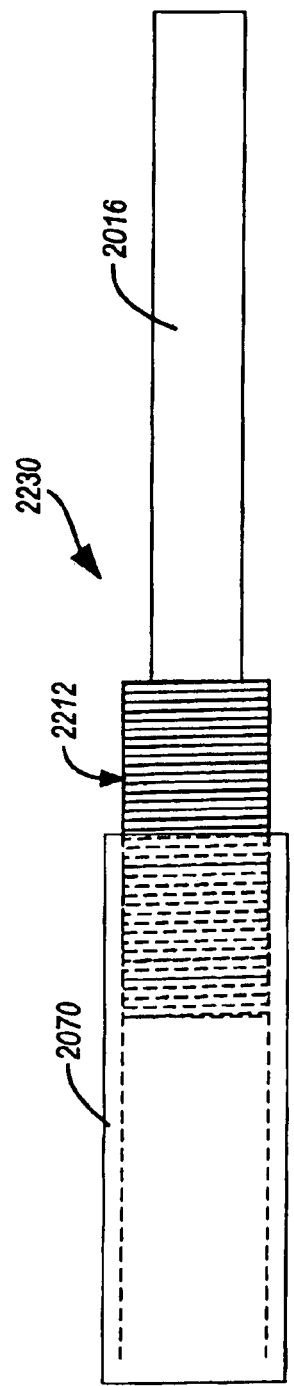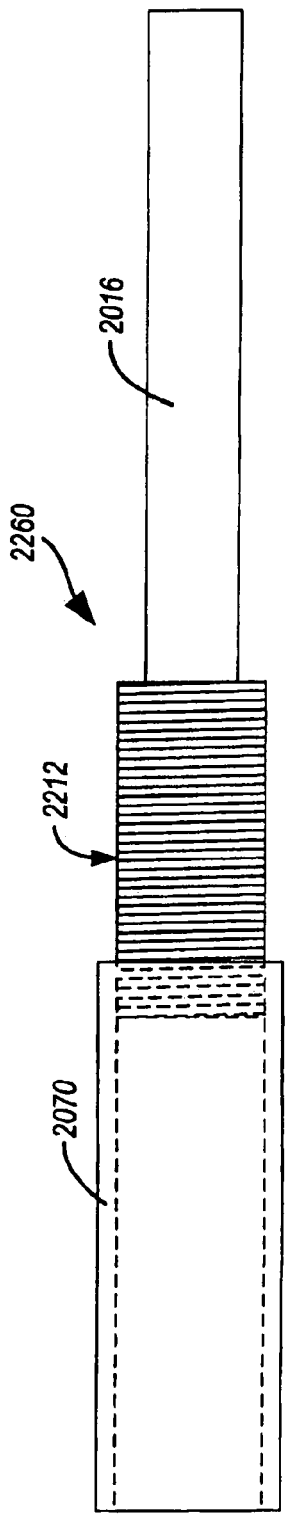

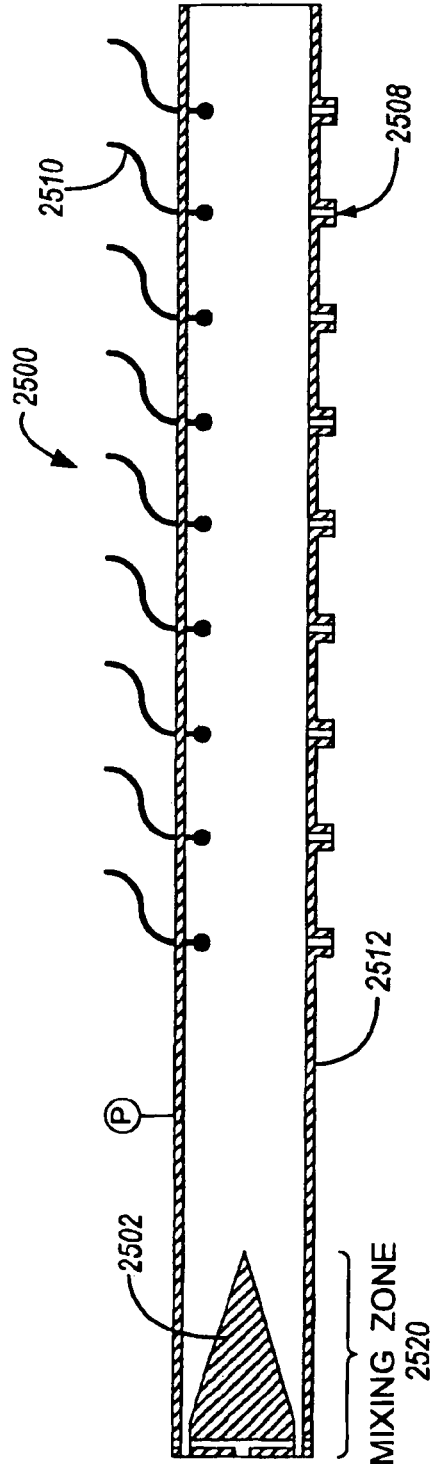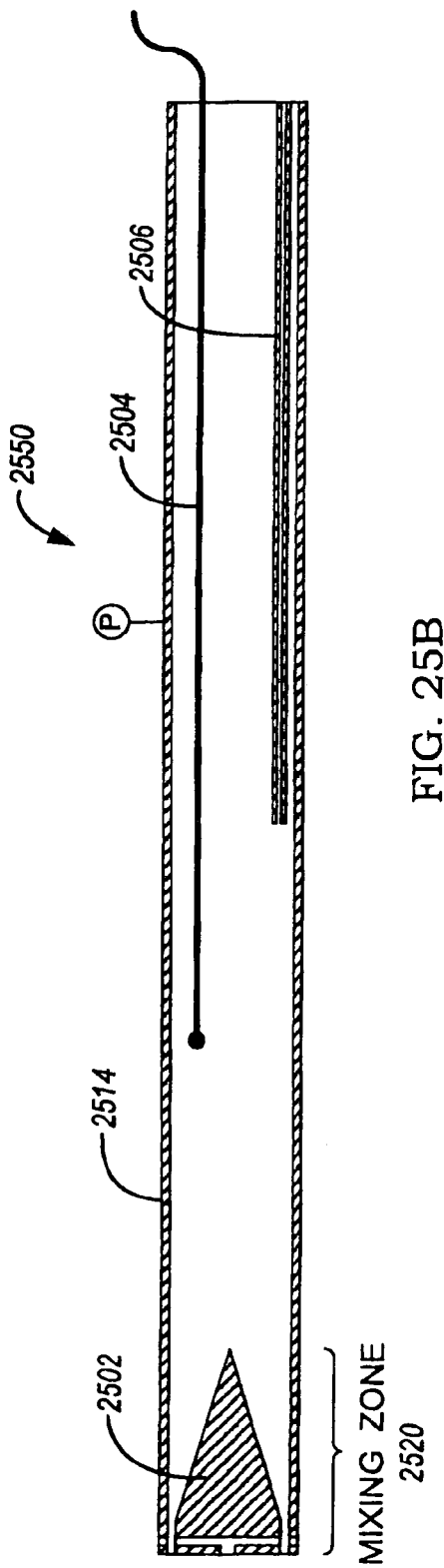

METHOD FOR DIRECT-OXYGENATION OF ALKANE GASES

CROSS-REFERENCE TO RELATED APPLICATIONS

This application is a divisional of U.S. patent application Ser. No. 11/685,867, filed Mar. 14, 2007, now U.S. Pat. No. 7,456,327 which is a continuation-in-part of International Applications PCT/US2007/004557, filed Feb. 19, 2007; PCT/US2007/004297, filed Feb. 19, 2007; and PCT/US2007/004185, filed Feb. 19, 2007. Each of International Applications PCT/US2007/004557; PCT/US2007/004297; and PCT/US2007/004185 is a continuation-in-part of U.S. application Ser. Nos. 11/526,824, filed Sep. 25, 2006; 11/446,371, filed Jun. 2, 2006; now abandoned 11/432,692, filed May 11, 2006; and 11/351,532, filed Feb. 10, 2006. Each of U.S. application Ser. Nos. 11/526,824; 11/446,371; 11/432,692; and 11/351,532 is a continuation- in-part of U.S. application Ser. No. 11/319,093, filed Dec. 27, 2005. The disclosures of the above applications are hereby incorporated by reference.

BACKGROUND OF THE INVENTION

The present invention relates to a method of reacting natural gas and oxidant under conditions to optimize the formation of desired alkyl oxygenates (especially, methanol). More specifically, the embodiments are for reacting a $C_1$-$C_4$ alkane (methane, ethane, propane, and butane) into an alkyl oxygenate, and, more particularly in a focal application, for direct oxidation (under partial oxidation conditions) conversion of methane into methanol.

The current industrial practice for methanol production is a two-step, Fischer-Tropsch type chemical process. The first step is the endothermic reforming of methane from natural gas to carbon monoxide and hydrogen, followed by a second step consisting of a solid-catalyzed reaction between carbon monoxide and hydrogen to form methanol. This technology is energy intensive and the process economics are unfavorable for all but very large scale methanol plants.

Various methods and apparatuses for the conversion of methane into methanol are known. It is known to carry out a vapor-phase conversion of methane into a synthesis gas (mixture of CO and $H_2$) with its subsequent catalytic conversion into methanol as disclosed, for example, in Karavaev M. M., Leonov B. E., et al "Technology of Synthetic Methanol'", Moscow, "Chemistry" 1984, pages 72-125. However, in order to realize this process it is necessary to provide complicated equipment, to satisfy high requirements for the purity of the gas, to spend high quantities of energy for obtaining the synthesis gas and for its purification, and to have a significant number of intermittent stages from the process. Also, for medium and small enterprises with the capacity of less than 2,000 tons/day it is not economically feasible.

Russian Patent No. 2,162,460 includes a source of hydrocarbon-containing gas, a compressor and a heater for compression and heating of the gas, and a source of oxygen-containing gas with a compressor. It further includes successively arranged reactors with alternating mixing and reaction zones and a means to supply the hydrocarbon-containing gas into a first mixing zone of the reactor and the oxygen-containing gas into each mixing zone, a recuperative heat exchanger for cooling of the reaction mixture through a wall by a stream of cold hydrocarbon-containing gas of the heated hydrocarbon-containing gas into a heater, a cooler-condenser, a partial condenser for separation of waste gases and liquid products with a subsequent separation of methanol, a pipeline for supply of the waste gas into the initial hydrocarbon-containing gas, and a pipeline for supply of waste oxygen-containing products into the first mixing zone of the reactor.

In this apparatus, however, fast withdrawal of heat from the highly exothermic oxidation reaction of the hydrocarbon-containing gas in not achievable because of the inherent limitations of the heat exchanger. This leads to the need for reduction in the quantity of supplied hydrocarbon-containing gas and, further, it reduces the degree of conversion of the hydrocarbon-containing gas. Moreover, even with the use of oxygen as an oxidizer, it is not possible to provide an efficient recirculation of the hydrocarbon-containing gas due to the rapid increase of the concentration of carbon oxides. A significant part of the supplied oxygen is wasted for oxidation of CO into $CO_2$, and thereby additionally reduces the degree of conversion of the initial hydrocarbon-containing gas to useful products and provides a further overheating of the reaction mixture. The apparatus also requires burning an additional quantity of the initial hydrocarbon-containing gas in order to provide the utility needs of a rectification of liquid products. Since it is necessary to cool the gas-liquid mixture after each reactor for separation of liquid products and subsequent heating before a next reactor, the apparatus is substantially complicated and the number of units is increased.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in liquid product rectification stage.

Other patent documents such as U.S. Pat. Nos. 2,196,188; 2,722,553; 4,152,407; 4,243,613; 4,530,826; 5,177,279; 5,959,168 and International Publication WO 96/06901 disclose further solutions for transformation of hydrocarbons.

There is also a need for a one step process that is also suitable for small-scale processing, overcoming process scale limitations of the Fischer Tropsch method, and also making "stranded gas" a valuable commodity. This approach makes use of a homogeneous, gas phase partial oxidation reaction, carried out by contacting natural gas and an oxidant, with the oxidant as the limiting reagent. The most abundant products are methanol and formaldehyde, coming from methane, the principal component of natural gas. Smaller amounts of ethanol and other oxygenated organic compounds are formed by oxidation of methane, ethane, propane, and higher hydrocarbons that are all minor constituents of natural gas. These reaction products are all liquids, and are transportable to a central location for separation and/or subsequent use as fuels or as chemical intermediates. A central feature of such processes is that the process chemistry can be executed in the field at remote locations.

U.S. Pat. No. 4,618,732 ("Direct conversion of natural gas to methanol by controlled oxidation" to Gesser, et al.) describes a process for converting natural gas to methanol. The selectivity for methanol is indicated as resulting from careful premixing of methane and oxygen along with the use of glass-lined reactors to minimize interactions with the processing equipment during the reaction. The need for mixing prior to entering a reactor for reaction initiation is indicated in the following extract:

"The mixing of gases preferably takes place in a pre-mixing chamber or "cross" of relatively small volume and then pass through a short pre-reactor section before entering the heated reaction zone. However, when mixing gases at high pressure in a relatively small volume, laminar flow often takes place with the oxygen or air forming a narrow homogeneous stream within the general flow of natural gas. The oxygen or air has little chance of becoming dispersed throughout the reaction stream prior to reaching the reaction zone. Without wishing to be bound by theory, when this takes place it is postulated that the natural gas is oxidized initially to methanol which is further oxidized, at the periphery of the oxygen stream, i.e. in an oxygen-rich environment, to higher oxidation products."

U.S. Pat. No. 4,618,732 to Gesser also emphasizes the need to keep the reaction from initiation until mixing is completed (—"mixing oxygen and natural gas prior to their introduction into a reactor").

U.S. Pat. No. 4,982,023 ("Oxidation of methane to methanol" to Han, et al.) brings forth that a plurality of reactions is occurring in the direct oxygenation of methane to methanol. In this regard, U.S. Pat. No. 4,982,023 indicates some consideration of reaction-kinetics issues in the discussion of that patent's subject matter:

"The mechanism of methanol formation is believed to involve the methylperoxy radical ($CH_3OO$) which abstracts hydrogen from methane. Unfortunately, up until now, the per pass yields have been limited. This limited yield has been rationalized as resulting from the low reactivity of the C—H bonds in methane vis-a-vis the higher reactivity of the primary oxygenated product, methanol, which results in selective formation of the deep oxidation products CO and $CO_2$ when attempts are made to increase conversion."

U.S. Pat. No. 4,982,023 also makes it clear that methane and oxygen are to be premixed prior to reaction as noted in the following extract: " . . . natural gas and the oxygen or air are kept separate until mixed just prior to being introduced into the reactor. However, if desired, the oxygen and natural gas may be premixed and stored together prior to the reaction".

Unfortunately, laboratory results regarding methanol selectivity and single pass yield for non-catalyzed direct oxygenation of methane to methanol have not been reliably duplicated in scaling the reaction technology to manufacturing-sized systems. The need for an efficient and low cost method for enabling non-catalyzed direct oxygenation of methane to methanol continues to be unfulfilled.

SUMMARY

It is accordingly an object of the present invention to provide a method for manufacturing at least one alkyl oxygenate (e.g., without limitation, ethanol, formaldehyde, and/or ethanol) through partial oxidation reacting of alkane (e.g., without limitation, methane, ethane, propane, and butane) from an alkane-containing gas feed stream and of oxygen from an oxygen-containing gas feed stream. The method comprises providing a reactor system having an injectively-mixed backmixing reaction chamber in fluid communication with a tubular-flow reactor; feeding the alkane-containing feed stream and the oxygen-containing feed stream to the injectively-mixed backmixing reaction chamber; inducing alkyl free radical formation in the injectively-mixed backmixing reaction chamber to yield an injectively-mixed backmixing reaction chamber product stream comprising oxygen, the alkane, and at least a portion of the alkyl free radicals; feeding the injectively-mixed backmixing reaction chamber product stream to a tubular-flow reactor; and reacting the injectively-mixed backmixing reaction chamber product stream into the alkyl oxygenate in the tubular-flow reactor.

In one embodiment, the feeding of the alkane-containing feed stream and the oxygen-containing feed stream injectively intermixes the alkane-containing feed stream and the oxygen-containing feed stream to thereby turbulently agitate the injectively-mixed backmixing reaction chamber.

In another embodiment, the feeding of the injectively-mixed backmixing reaction chamber product stream fluidly conveys the backmixing reaction chamber product stream through a flow restriction baffle.

In one aspect, the reactor system has a space-time for the inducing and the reacting, respective to a combined feed rate of the alkane-containing feed stream and the oxygen-containing feed stream, of not greater than 40 seconds.

In yet another embodiment, the tubular-flow reactor has a tubular-flow reactor input and a tubular-flow reactor output, the method further comprises quenchably cooling the tubular-flow reactor with a cooling gas stream received from a cooling gas input disposed at a location between the tubular-flow reactor input and the tubular-flow reactor output. In one aspect of this, the cooling is achieved by axially adjusting the location of the cooling gas input during operation of the tubular-flow reactor.

In various embodiments, the tubular-flow reactor discharges a reaction product stream from the tubular-flow reactor output, and the method further comprises scrubbing the reaction product stream with a liquid absorbent to remove methanol from the reaction product stream. In other aspects of various embodiments, the absorbent further absorbs carbon dioxide and/or formaldehyde from the reaction product stream. In yet another aspect of various embodiments, the method further comprises recycling a recycle stream from the scrubber to the alkane-containing feed stream (preferably to provide a weight percentage proportion of from about 4:5 to about 20:21 of alkane in the alkane-containing feed stream).

In yet another embodiment, the injectively-mixed backmixing reaction chamber has a backmixing reaction chamber housing and a bulkhead in slideably-sealed interface to the backmixing reaction chamber housing, the injectively-mixed backmixing reaction chamber has an injectively-mixed backmixing reaction chamber internal volume defined by the backmixing reaction chamber housing and by the bulkhead, and the backmixing reaction chamber housing has a housing portion in opposite disposition to the bulkhead. In these embodiments, the inducing further comprises either (a) slideably moving the bulkhead during real-time operation of the reactor system to progress within the injectively-mixed backmixing reaction chamber housing toward the housing portion to commensurately diminish the injectively-mixed backmixing reaction chamber internal volume, or (b) slideably moving the bulkhead during real-time operation of the reactor system within the injectively-mixed backmixing reaction chamber housing to retract away from the housing portion to thereby commensurately expand the injectively-mixed backmixing reaction chamber internal volume.

In yet another embodiment, the feeding of the alkane-containing feed stream further comprises pressurizing the alkane-containing gas feed stream with a centrifugal blower prior for input to the injectively-mixed backmixing reaction chamber.

The novel features that are considered as characteristic for the present invention are set forth in particular in the appended claims. The invention itself, both as to its construction and its method of operation together with additional objects and advantages thereof, will be best understood from the following description of specific embodiments when read in connection with the accompanying drawings.

BRIEF DESCRIPTION OF THE DRAWINGS

FIGS. 13A and 13B present cross section simplified views of details in modifying the internal volume of the injectively-mixed backmixing reaction chamber of FIG. 12;

FIGS. 15A and 15B present a cross section simplified view of a "hairbrush" fluid delivery insert for the injectively-mixed backmixing reaction chamber of the reactor system embodiments of FIGS. 12 and 20;

FIG. 16 presents a cross section simplified view of internal fluid passageways for the conical fluid delivery insert for the injectively-mixed backmixing reaction chamber of the reactor system embodiments of FIGS. 12 and 20;

FIGS. 18A and 18B present a cross section simplified view of details and positioning for one variable position quenching inlet of the reactor system embodiments of FIGS. 12 and 20;

FIGS. 19A and 19B present a series of temperature profiles for the tubular-flow reactor of the reactor system embodiments of FIGS. 12 and 20;

FIGS. 22A-22C show axial positioning detail for the interface between the injectively-mixed backmixing reaction chamber and the tubular-flow reactor of the FIG. 20 reactor system embodiment;

FIGS. 25A and 25B show views of tubular-flow reactor systems having injectively-mixed entry zones, multi-position quenching, and multi-position temperature sensing.

DESCRIPTION OF THE PREFERRED EMBODIMENTS

The following definitions and non-limiting guidelines must be considered in reviewing the description of this invention set forth herein.

The headings (such as "Introduction" and "Summary") and sub-headings (such as "Amplification") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in compositions, materials, devices, and methods of this invention.

The examples and other embodiments described herein are exemplary and not intended to be limiting in describing the full scope of compositions and methods of this invention.

Equivalent changes, modifications and variations of specific embodiments, materials, compositions and methods may be made within the scope of the present invention, with substantially similar results.

The embodiments relate to direct oxygenation conversion of at least one $C_1$-$C_4$ alkane into as least one alkyl oxygenate. The direct oxygenation conversion of methane into methanol is a focal conversion goal of the technology.

Figure 1:
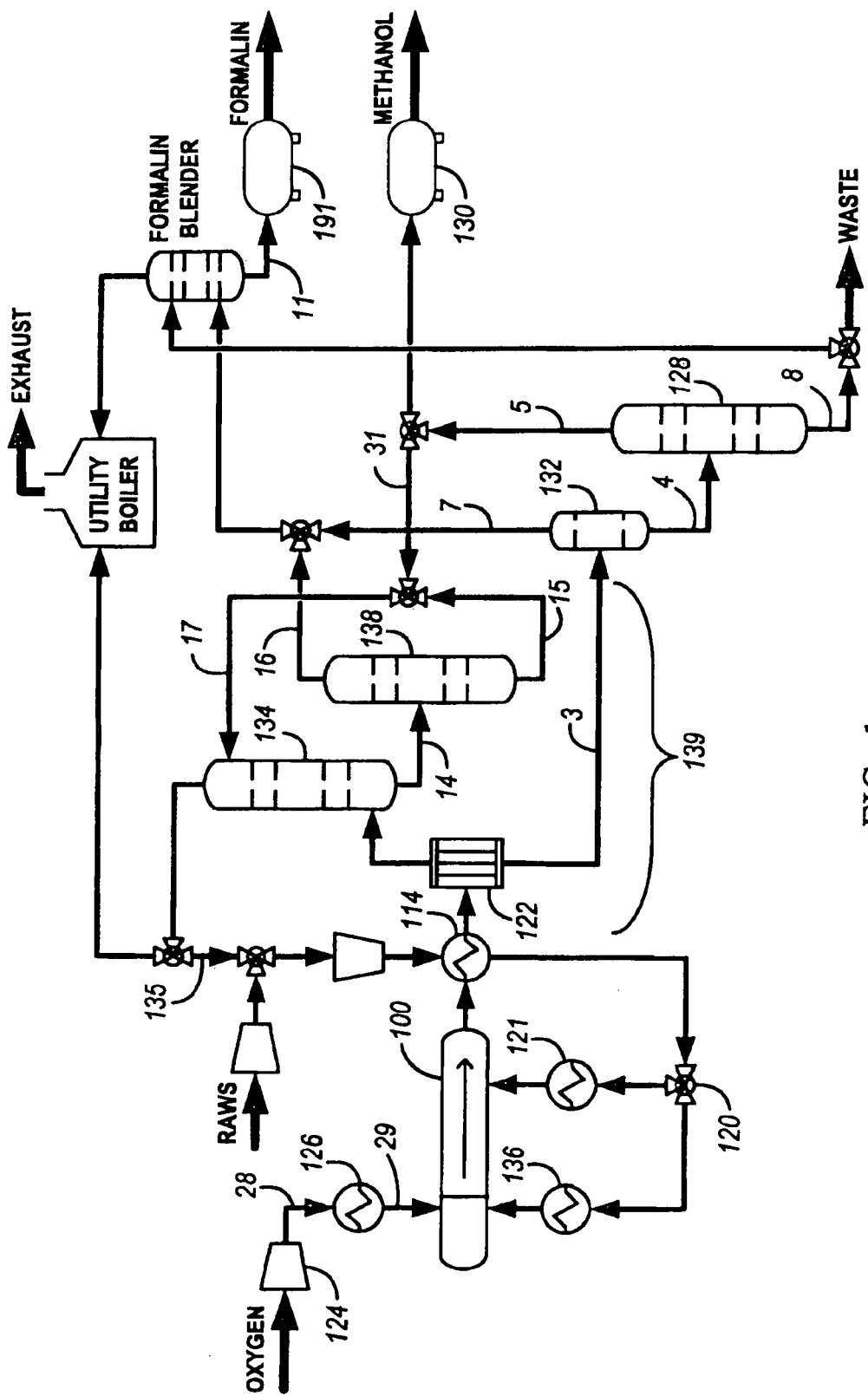
FIG. 1 schematically shows a system of an apparatus for producing alkyl oxygenate (e.g., without limitation, methanol) in accordance with the present teachings.

One apparatus for producing methanol in accordance with the present invention has a reactor 100 facilitating a gas phase oxidation of a hydrocarbon-containing gas as shown in FIG. 1. In overview of reactor 100, a heated hydrocarbon-containing gas stream (from valve 120 and heater 136) and an oxygen-containing gas from line 29 are introduced into reactor 100. As explained in detail below, the oxygen-containing gas preferably has greater than 80% oxygen content to reduce the accumulation of inert gases by the recycling process.

The reactor 100 further optionally receives a quenching cold hydrocarbon-containing gas stream from valve 120 and heat exchanger 121 for reducing the temperature of reaction during operation of the apparatus.

The apparatus has a device 114 for cooling the reaction product stream mixture before separation. Additionally, partial condenser 122 incorporates a gas-liquid heat exchanger to further reduce the temperature of the products. The condenser 122 separates $H_2O$ and alcohols from a hydrocarbon-$CO_2$ mixture. The partial condenser 122 is preferably isobaric, as opposed to isothermal, to avoid pressure losses. The reaction product stream enters, and a liquid stream and gaseous stream exit condenser 122.

Block 139 represents equipment that is configured to separate contaminants and products from a hydrocarbon-containing recycle gas component. In this regard, the equipment 139 is configured to remove $CO_2$ from the reduced product stream. The equipment 139 can take the form of a purge valve, absorber, membrane separator, or an adsorber. It is envisioned the equipment 139 can be used to regulate the percentage of other non-reactive components such as $N_2$ with, for example, a purge valve.

In the event the system is configured to recover formaldehyde, the gaseous reduced product stream leaves the isobaric condenser 122 and is passed to the scrubber 134. Other potential methods that can be utilized use materials such as various amines known to remove $CO_2$ and formaldehyde.

To fulfill the minimum absorption requirements, modification of the flow rate of methanol or operating temperature of the scrubber column can be used. If it is desirable to operate at extremely low absorbent flow rates, then a lower temperature can be utilized, for example 0° C. If it is desirable to operate at ambient temperatures or temperatures achievable via cooling water, then a high flow rate can be utilized, for example, ten times that of the flow rate for 0° C. In either scenario, the pregnant methanol absorbent stream 14 is completely regenerated by the formaldehyde distillation column 138. Optionally, the stream 14 from the scrubber 134 can be passed through the condenser 122 to provide cooling of the product stream and preheating of the methanol recycle to improve the energy efficiency of the formaldehyde distillation column 138.

The reactor 100 is connected with a compressor 124 and heater 126 for supply of compressed and heated oxygen-containing gas. The raw hydrocarbon-containing gas is mixed with cleaned hydrocarbon gas from the scrubber 134 and is heated using a heater 136. In the event the raw hydrocarbons have a high $CO_2$ content, the raw hydrocarbons can be mixed with the reduced product hydrocarbon stream from the condenser 122 prior to the entry of the scrubber 134 for removal of contaminant gases prior to entering the reactor.

The apparatus further has a unit for rectification of methanol that includes a flash drum 132, rectification column 128, and a vessel 130 from which methanol is supplied to storage or further processing. This rectification column 128 is used to separate methanol (light-key component) from ethanol (heavy-key component) and water (non-key component). As before, it is desirable for a portion of the heavy key component to enter the distillate stream (as dictated by commercial specification for formalin). For methanol rectification, 99% or higher purity is typical, and 99.999% is achievable with multiple columns. Stream 4 enters the column and the distillate, stream 5, and bottoms, stream 8, exit the column in liquid phase. Stream 8 has some amount of ethanol (and perhaps methanol, if ultra pure methanol was produced) and will be used as the basis of the aqueous makeup of the commercial formalin stream (stream 11 and formalin storage 191). In this manner, some of the ethanol is recovered before the remainder is discarded in the liquid waste stream.

Disposed between the column 128 and the condenser 122 is a flash drum 132 for removal of $CO_2$ and formaldehyde from the liquid product stream. The purpose of the flash drum 132 is to drop the pressure to an appropriate level before entry into the methanol rectification column 128 and to substantially remove any dissolved gases, typically $CO_2$ and formaldehyde, from the liquid product stream.

In operation, the raw hydrocarbon-containing gas stream with a methane content for example up to 98% and the reduced hydrocarbon product stream are supplied from an installation for preparation of gas or any other source to the heater 136, in which it is heated to temperature 430-470° C. The heated hydrocarbon-containing gas is then supplied into reactor 100. Compressed air with pressure, for example, of 7-8 MPa and with a ratio 80% to 100% and, preferably, 90% to 95% oxygen is supplied by the compressor 124 also into reactor 100. Oxidation reaction of methane to methanol and/ or formaldehyde takes place in reactor 100. Between 2% and 3% $O_2$ of the total volume of the reactants are reacted with the heated hydrocarbon-containing gas stream as previously described. To limit the amount of $N_2$ within the system, for example to less than 30%-40%, or reduce the requisite size of the purge stream to achieve the same, the $O_2$ stream is preferably substantially pure, thus limiting the amount of $N_2$ entering the system.

An optional second stream of cold (or, in other words, a lower temperature coolant than the gases) coolant in the reactor is supplied into reactor 100 as previously outlined. This stream is regulated by the regulating device (valve) 120, that can be formed as a known gas supply regulating device, regulating valve, or the like. This cold stream can be, for example, composed of a raw hydrocarbon stream, a recycled stream, or a portion or combination of the two. The regulator is configured to adjust the volume or pressure of cold hydrocarbon-containing gas based on system parameters such as, but not limited to, pressure, temperature, or reaction product percentages at a location further down-stream in the system.

The coolant, which is supplied from a coolant source, functions to reduce the temperature of the partially oxidized methane to reduce the continued oxidation or decomposition of formaldehyde. This coolant can be any material that can easily be separated from the reaction product stream. For example, as better described below, the coolant can be an unheated hydrocarbon or methane containing gas stream.

Preferably, the coolant can be any non-oxidizing material easily separated from the reaction products. In this regard, the coolant can be gaseous, an aerosol, or misted liquid of, example, $CO_2$, formaldehyde, methanol, water, and/or steam. It is additionally envisioned that the coolant can further be a mixture of recycled reaction products, water, steam, and/or raw hydrocarbon gases.

Depending on the intended mode of operation of the apparatus, in particular the intended production of methanol or methanol and formaldehyde, the reaction mixture is subjected to the reaction in the reactor without the introduction of the cold hydrocarbon-containing gas if it is desired to essentially/exclusively produce methanol. The introduction of the cold hydrocarbon-containing gas is used when methanol and formaldehyde are both desired as products. By introduction of the cold hydrocarbon-containing gas, the temperature of the reaction is reduced, for example by 30-90° Celsius, so as to preserve the content of formaldehyde in the separated mixture by reducing the decomposition of the formaldehyde into $CO_2$.

The reaction mixture is supplied into the heat exchanger 114 for transfer of heat to the reactor input stream from the reaction mixture exiting the reactor, and, after further cooling, is supplied to partial condenser 122. Separation of the mixture into high and low volatility components (dry gas and raw liquid, respectively) is performed in the partial condenser 122 that may absorb at least some of the formaldehyde into the raw liquid stream as desired. The dry gas is forwarded to a scrubber 134, while the raw liquids from the condenser 122 are supplied to the flash drum 132.

Scrubber 134 functions to remove the $CO_2$ and formaldehyde from the dry gas stream. In this regard, the scrubber 134 uses both $H_2O$ and methanol at between 7-8 MPa pressure and between about 0° C. and about 50° C. to absorb $CO_2$ and formaldehyde. Once the $CO_2$ and formaldehyde are removed, the reduced stream of hydrocarbon gas is recycled by mixing the reduced stream with the raw hydrocarbon-containing gas stream either before or within the reactor, as desired. The raw hydrocarbon and reduced streams, individually or in combination, are then inputted into reaction chamber 100 at after being heated by heat exchanger 116 and heater 136 as previously described.

Rectification column 138 is used to separate carbon dioxide (non-key component) and formaldehyde (light-key component) from methanol (heavy-key component) and water (non-key component). The pregnant methanol steam, stream 14, enters rectification column 138 and is separated into formaldehyde distillate stream 16 and bottoms stream 15. Some amount of methanol in the distillate stream is desirable since methanol is used as a stabilizer for the production of commercial grade formalin (6-15% alcohol stabilizer, 37% formaldehyde, and the balance being water). By allowing a portion of the heavy key component into the distillate stream the separation is more easily achieved; furthermore, process losses typically experienced during absorbent regeneration are subsequently nullified as methanol within the distillate is used for formalin production. Stream 15 is supplemented by stream 31 so as to replace any methanol that was transferred to the distillate stream, stream 16. Combining stream 31 and stream 15 results in stream 17, which then returns to the scrubber 134 as regenerated methanol absorbent. Meanwhile, the formaldehyde distillate, stream 16, combines with the vapors from flash drum 132, stream 7, to form a mixture of formaldehyde, methanol, and carbon dioxide.

The formaldehyde, water, methanol and $CO_2$ removed by scrubber 134 are passed to formaldehyde rectification column 138. Column 138 removes formaldehyde and $CO_2$ from the methanol-water stream. Small amounts of methanol are combined with produced methanol and are inputted into the scrubber 134 to remove additional amounts of $CO_2$ and formaldehyde from the reduced hydrocarbon stream.

Free or non-aqueous formaldehyde is allowed to remain in the gas phase by operation of the isobaric condenser 122. The liquid methanol product stream, or raw liquids, therefore comprise methanol, ethanol, and water insofar as formaldehyde remains in the gaseous stream. In this case, the liquid stream exiting the isobaric condenser 122 can bypass the formaldehyde rectification portion of the process and enter the methanol rectification column after having optionally passed through the flash drum 132.

Figure 2:
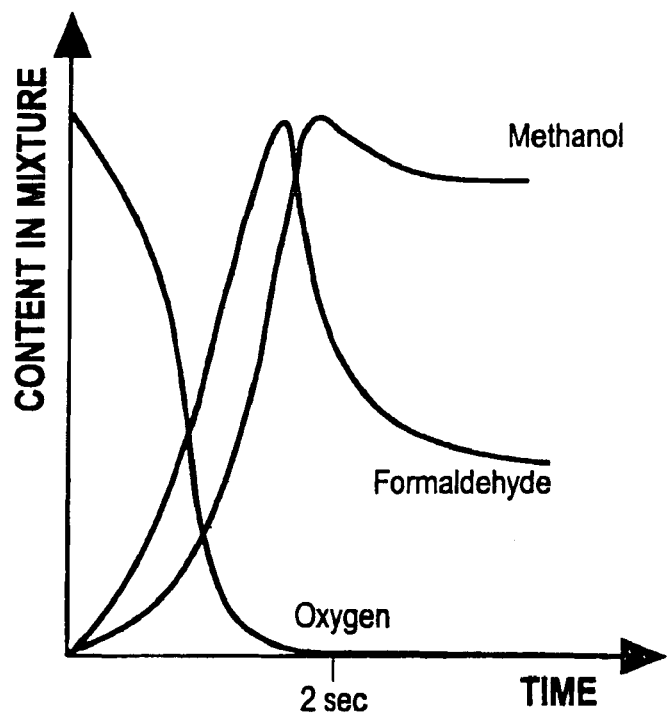
FIGS. 2 and 3 are views illustrating concentrations of oxygen, formaldehyde, and methanol during reactions in accordance with the prior art and in accordance with the present invention correspondingly.
Figure 3:
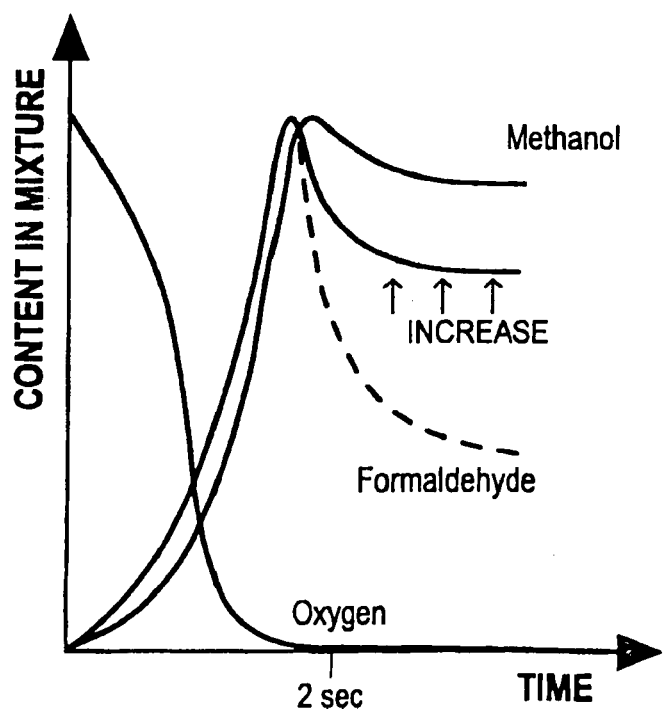

FIGS. 2 and 3 show diagrams of the concentration of oxygen, formaldehyde and methanol in reactions without cooling and with cooling, respectively.

As can be seen from FIG. 2, approximately after 2 sec of reaction time, the oxygen is essentially completely reacted. At this moment, the reaction temperature reaches its maximum and methanol and formaldehyde are produced in their respective proportions within the reaction mixture. Methanol is a more stable product at the end of the reaction and its concentration remains substantially stable after reaching its maximum concentration. Formaldehyde is less stable, and therefore with a temperature increase (the temperature increases until oxygen is essentially completely consumed) its concentration somewhat reduces.

In the reaction with the cooling shown in FIG. 3, via the introduction of cold gas when the formation of methanol and formaldehyde is completed, the temperature of a final period of the reaction is reduced so as to inhibit the decomposition of formaldehyde.

Figure 4:
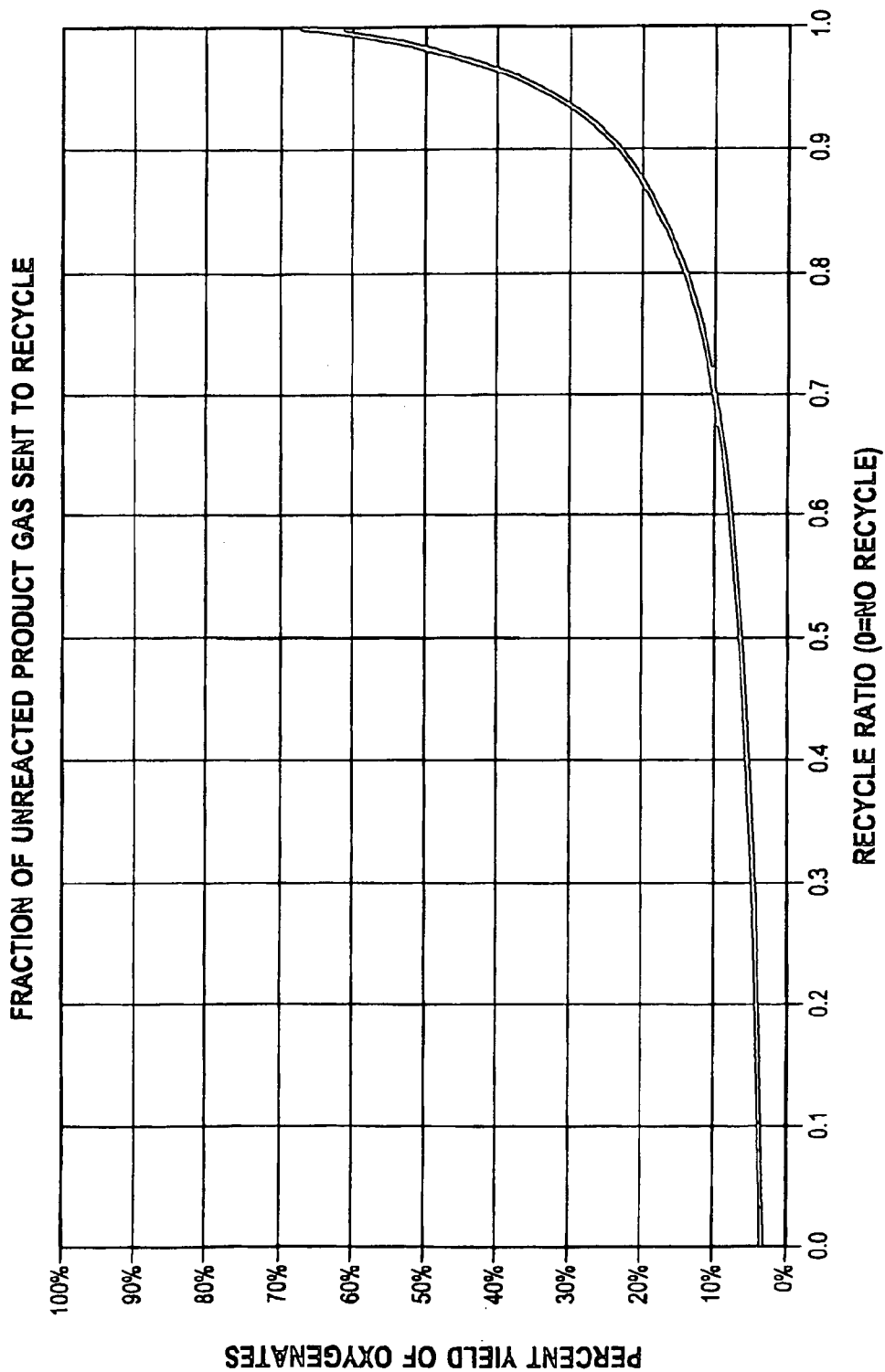
FIG. 4 represents a graph depicting the yield oxygenates of the system as a function of recycle ratio.

FIG. 4 represents a graph depicting the yield of oxygenates for the system as a function of the fraction of hydrocarbon gas recycled. Shown is a graph depicting the use of Michigan Antrim gas having 97% $CH_4$ and 1% $N_2$. In this regard, the graph shows a significant increase in overall product yield using the same input stream and with little increase in capital costs. As the system efficiently manages pressure and integrates process energy usage, energy requirements are minimized, thus increasing the overall system economics.

Figure 5:
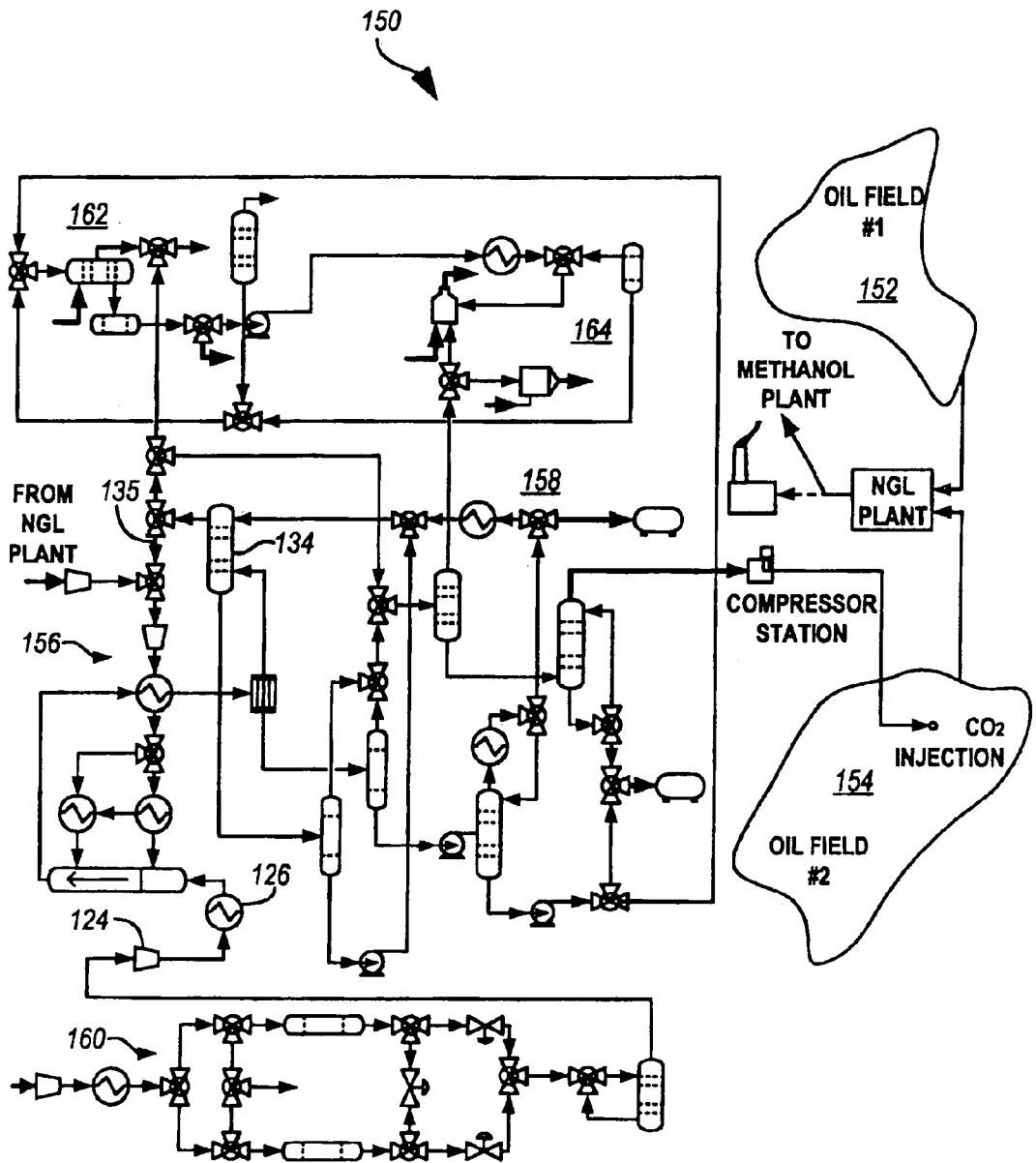
FIG. 5 represents an alternate $C_1$-$C_4$ alkane to alkyl oxygenate plant according to the teachings of the present invention.

FIG. 5 represents an alternate methane to methanol plant 150. The plant 150 is positioned to process methane from gas being discharged from either a combined oil and gas field 152 or the gas field 154. The plant 150, which is preferably located in close proximity to the well bore, is generally formed of a gas processing plant 156, a liquid processing plant 158, and an oxygen producing plant 160. Additionally associated with the plant 150 are waste water treatment and utility plants 162 and 164.

Figure 6:
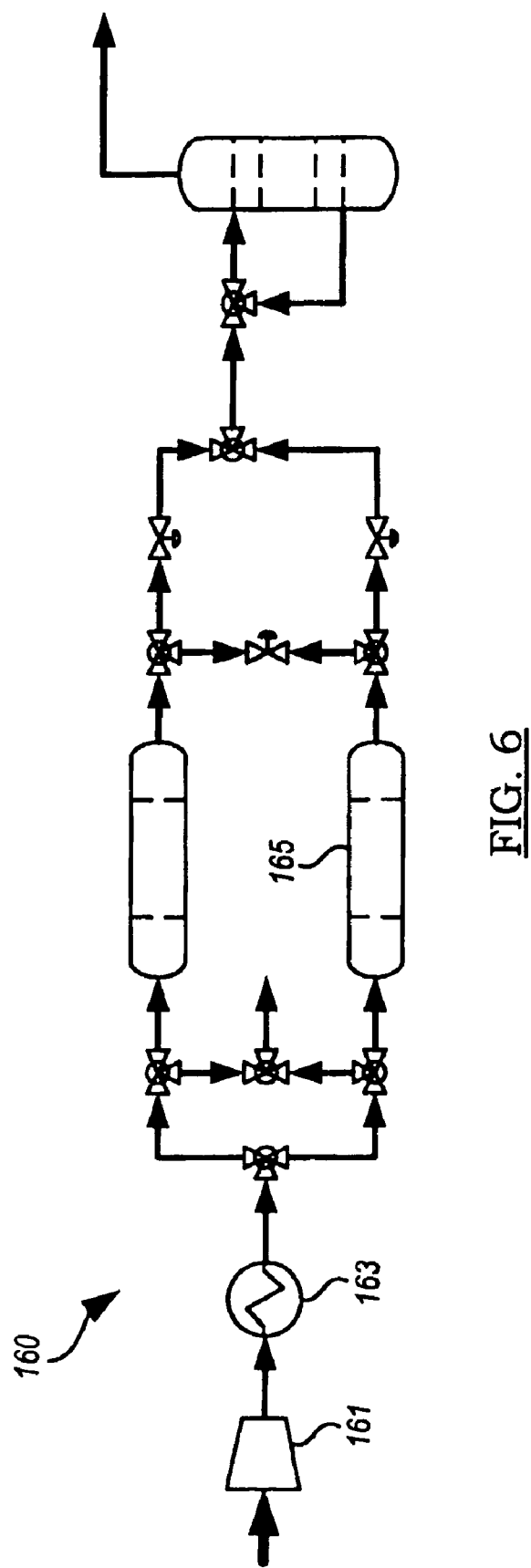
FIG. 6 represents an optional oxygen producing plant shown in FIG. 5.

As shown in FIG. 6, an optional oxygen producing plant 160 can be used to assist in the regulation of the partial oxidation of the hydrocarbon stream in the reactor 100. The oxygen producing plant 160 has a compressor 161 coupled to a heat exchanger 163 which functions to prepare the compressed oxygen for injection into a plurality of absorbers 165. After passing through the absorbers, the produced oxygen stream is compressed and forwarded directly to the reactor 100.

Figure 7:
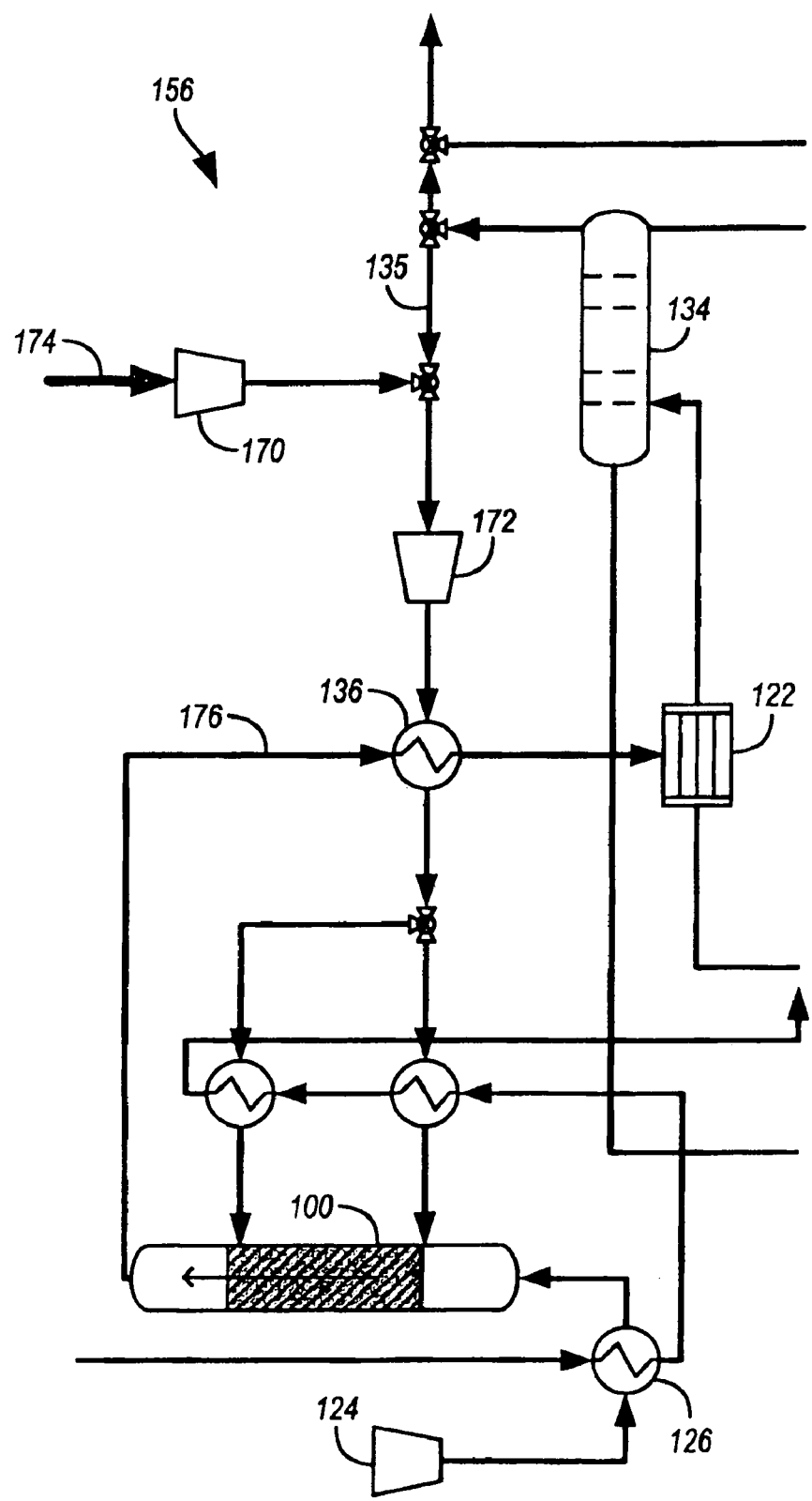
FIG. 7 depicts a gas processing portion of the plant shown in FIG. 5.

With general reference to FIG. 7, the gas processing portion of the plant 156 generally functions as described above (see FIG. 1). In this regard, the gas processing plant 156 has compressors 170 and 172 for raising the pressure of a cleaned incoming hydrocarbon stream 174. This stream 174 is then divided and reacted with oxygen in the reactor 100 to partially oxidize methane as described above. It is envisioned that the parameters such as time of reaction and temperature and pressure within the reactor can be adjusted to selectively control the amount of $CO_2$, $H_2O$, formaldehyde and methanol that are produced in the reactor 100. The reaction products 176 from the reactor are then transferred to the liquid processing plant 158.

Figure 8:
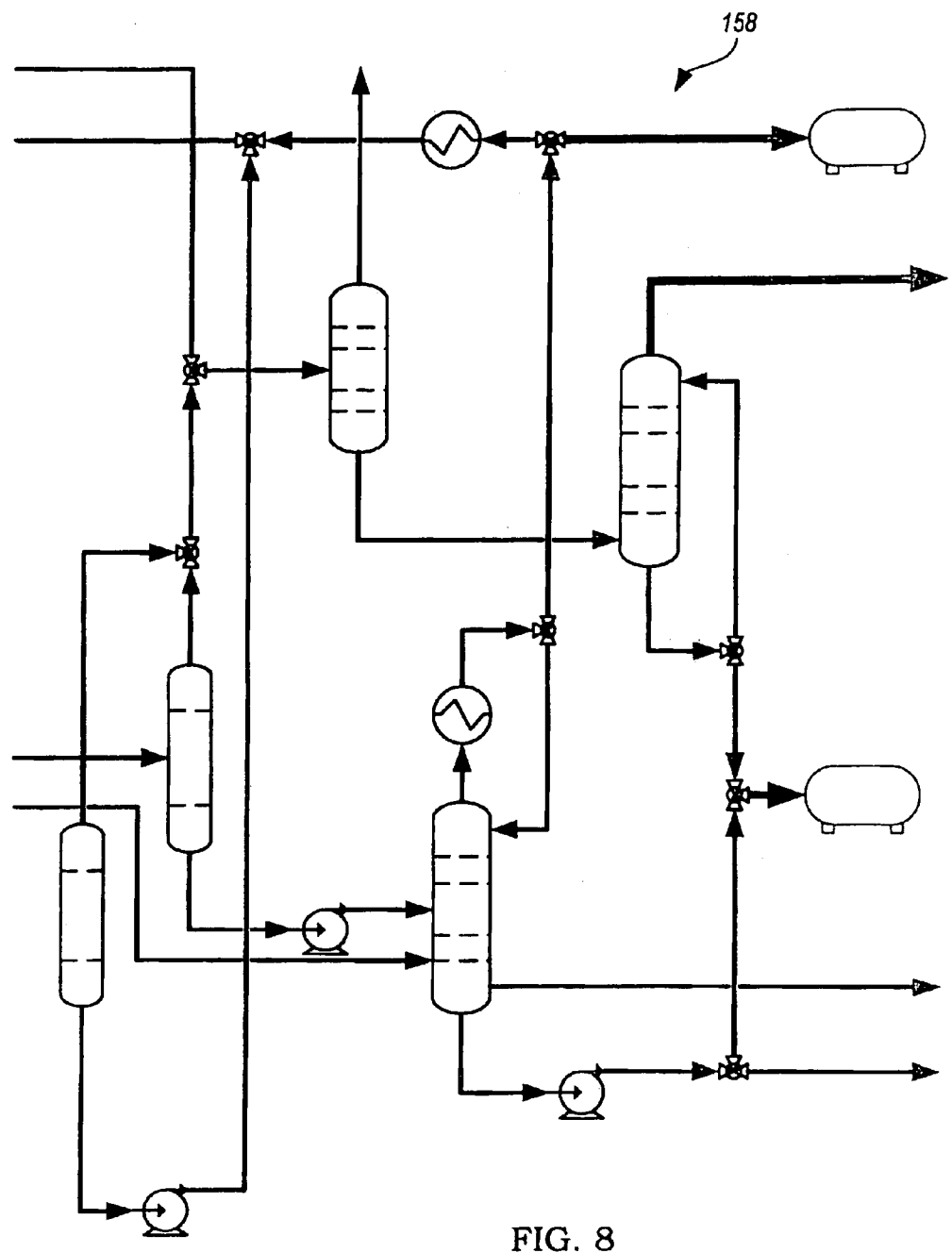
FIG. 8 represents the liquid processing portion of the plant shown in FIG. 5.

As shown in FIG. 8, the liquid processing plant 158 generally functions as described above to separate the methanol and formaldehyde from the reaction product stream 176. Shown are associated distillers, blenders and flash drums that are used to separate the constituent materials of the reaction product stream as described in detail above. Specifically, $CO_2$ is removed from the reaction product stream as are methanol and, if desired, formaldehyde. The scrubber 134 (see FIG. 5) prevents the accumulation of $CO_2$ and allows the physical capture of formaldehyde. The scrubber 134 can utilize a mixture of methanol and water to physically absorb formaldehyde and $CO_2$ from the hydrocarbon gas recycle loop 135. The efficiency of the scrubber 134, which can operate adequately without refrigeration, is made possible due to the high operating pressure of the recycle loop 135. This is opposed to cryogenically low temperatures utilized by traditional absorption processes. The gases enter the scrubber 134 as a "dirty" gas with some amount of formaldehyde and $CO_2$ present. These components will only be present in relatively dilute amounts, so the duty of the methanol absorbent is also relatively small.

As previously mentioned, it is envisioned that the output of the reactor can be selectively adjusted so as to minimize the amount of formaldehyde being produced by the gas process portion of the plant 156. While the $CO_2$ can be vented, it is specifically envisioned that the $CO_2$ from the reaction products can be injected, at a predetermined distance from the well, into the ground to increase the output of the well. In this regard, it is envisioned that the $CO_2$ can be injected at any appropriate distance from the well so as to allow for the increase of subterranean pressures to increase the gas or oil output of the well. Additionally, it is envisioned that the $CO_2$ can be injected into the casement of the wellbore or in the near-wellbore zone, to increase the output of the gas or oil and gas producing well.

While shown as a land based plant, it is specifically envisioned that the plant 150 can be associated with an off-shore oil rig. In this regard, the plant 150 would either be on the off-shore rig or would be a predetermined short distance from the rig, such as immediately adjacent to the off-shore rig on a floatable platform. In the case of an off-shore rig, which is producing natural gas, it is envisioned that the methanol converted from the methane containing hydrocarbon stream would be injected into a second portion of the methane containing hydrocarbon stream to improve the flow of the hydrocarbon stream from the off-shore oil well to land. This methanol is injected to reduce the formation of hydrates within the piping. The methanol associated with the natural gas would then be removed from the hydrocarbon containing stream after the stream reaches the shore.

It is further envisioned that any of the other reaction products, namely, $CO_2$, water or methanol can be injected directly into the hydrocarbon containing subterranean formations surrounding the platform or a land-based well. Specifically, it is envisioned that methanol can be injected into hydrate structures surrounding the well so as to increase the output of natural gas from a natural gas producing well.

Returning briefly to FIG. 5, it is envisioned that the $CO_2$ can be injected into one portion of the well while methanol or other reaction products can be injected into other portions of the well. In situations where the natural gas may be stranded or may have nitrogen contents of greater than 4%, facilities may be provided to manage nitrogen build-up in the recycle loop. When outputs of any particular well 152, 154 are low, it is envisioned that a single plant 100 having a truncated process can be used. In these situations, only portions of the facility related to the partial oxidation of the hydrocarbon stream and associated facilities to remove $CO_2$ will be used near the well.

Removed $CO_2$ can be collected, vented or reinjected into the ground. Immediately after removal of the natural gas and associated $CO_2$ by the scrubber, the remaining liquid products can be transported in liquid form from the well site to another location for separation of formaldehyde, methanol and water from the waste stream. In this regard, it is envisioned that a centralized liquid processing plant to finalize the processing of the liquid processes (158) can be located at a significant distance from the stranded natural gas locations. This allows for the use of a centralized liquid process facility 158. It is also envisioned that the conditions of the reactor can be adjusted to produce a liquid phase that contains a commercial grade of formalin.

Figure 9:
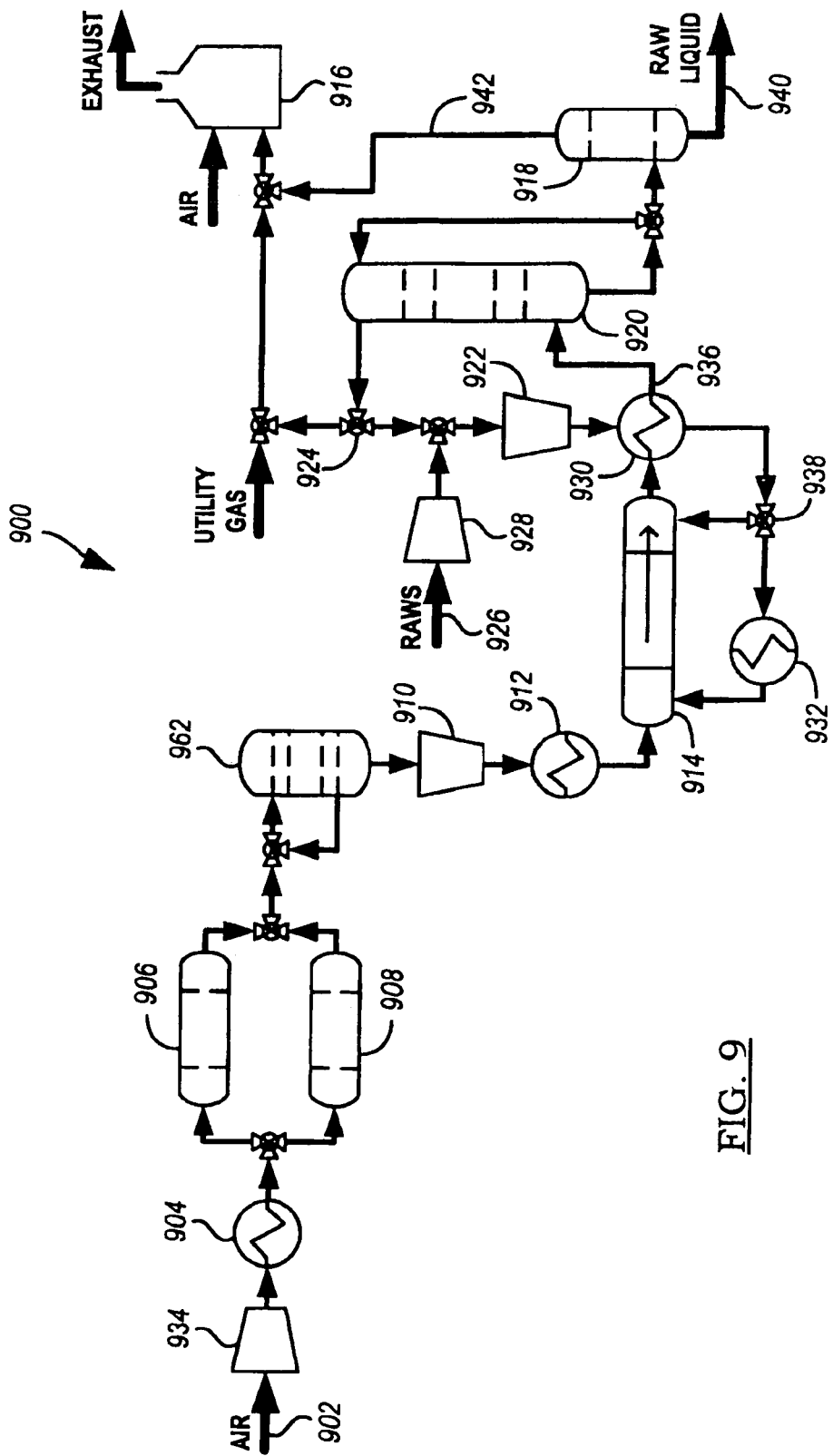
FIG. 9 represents another alternate $C_1$-$C_4$ alkane (e.g., without limitation, methane) to alkyl oxygenate (e.g., without limitation, methanol) plant according to the teachings of the present invention.

Another process embodiment 900 is presented in FIG. 9. Air 902 is input to compressor 934 and then cooled in heat exchanger 904 for delivery to one of nitrogen separator 906 or nitrogen separator 908. Oxygen feed is stored in tank 962 and compressed with compressor 910 for introduction as an oxygen-containing feed stream into reactor system 914 after heating in heater 912. Alkane-containing raw feed 926 (at least one $C_1$-$C_4$ alkane, primarily methane or natural gas) is compressed in compressor 928 and blended with scrubber 920 alkane recycle for further pressurization in compressor 922 and thermal cross exchange with reactor product stream reactor 936 in heat exchanger 930. The recycle stream preferably provides a weight percentage proportion of from about 4:5 to about 20:21 of alkane in the alkane-containing feed stream to reactor 914. In one embodiment, where scrubber 920 is pressurized to a pressure on the order of reactor system 914 (see FIGS. 12 to 24B and the accompanying text for further detail in reactor designs for reactor system 914), compressor 922 can be a centrifugal blower (non-positive displacement compressor). After thermal cross exchange with reactor product stream reactor 936 in heat exchanger 930, the combined raw alkane and recycle stream is heated in heat exchanger 932 to provide an alkane-containing feed stream to reactor system 914. Embodiments of reactor system 914 are further described in FIGS. 12-24B. Scrubber 920 operates to absorb carbon dioxide and alkyl oxygenates (for example, without limitation, methanol, ethanol, and formaldehyde) while providing a recycle stream for combination with fresh alkane to provide a feed stream to compressor 922. A purge at valve 924 removes non-reactive inerts (e.g., without limitation, nitrogen) from the reactor-scrubber process loop to augment efficient use of reactor system 914. A cooling quench to reactor system 914 is also optionally enabled from valve 938. Liquid bottoms from scrubber 920 are forwarded to flash drum 918 where overhead steam 942 separates from product stream 940 (comprising for example and without limitation, methanol, ethanol, and formaldehyde). Furnace or thermal oxidizer 916 oxidizes waste gases for discharge to the atmosphere. Process 900 is useful for providing a liquid material for further processing at another location into purified alkane oxygenates or for providing an alkane oxygenate blend useful for a fuel or other similar use where exact purity is not critical.

Figure 10:
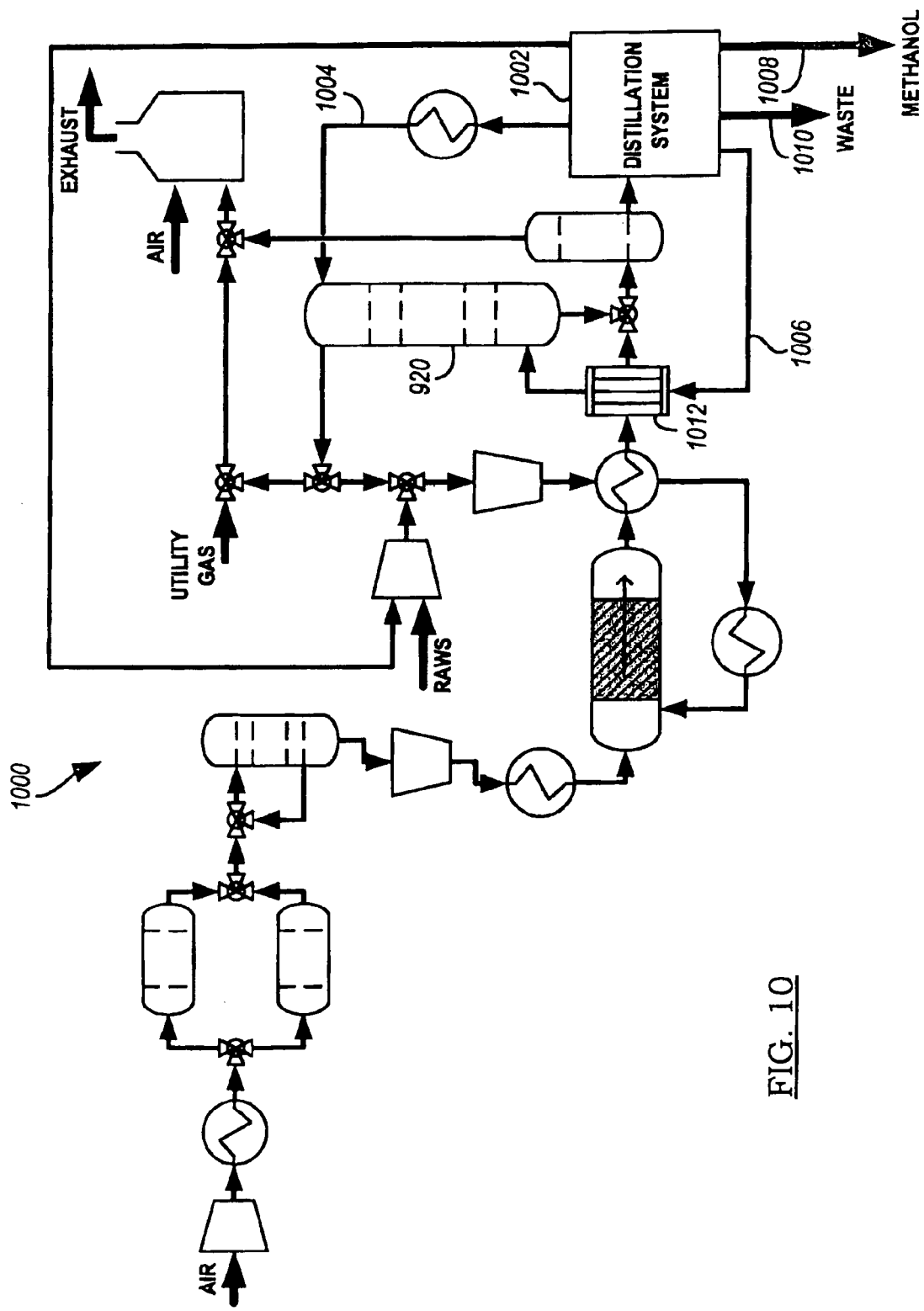
FIG. 10 represents yet another alternate $C_1$-$C_4$ alkane (e.g., without limitation, methane) to alkyl oxygenate (e.g., without limitation, methanol) plant according to the teachings of the present invention.

FIG. 10 shows another process embodiment 1000 with a front end process loop essentially similar to process 900 presented in FIG. 9, but incorporating an in-situ distillation system 1002 for separating methanol in steam 1004 (for absorbent in the scrubber), purified water in stream 1006 for use in knockdown drum 1012, and generation of purified methanol 1008 and waste stream 1010. Knockdown drum 1012 provides initial separation of liquid from the reactor product stream prior to the introduction of the remainder of the reactor product stream into the scrubber.

Figure 11:
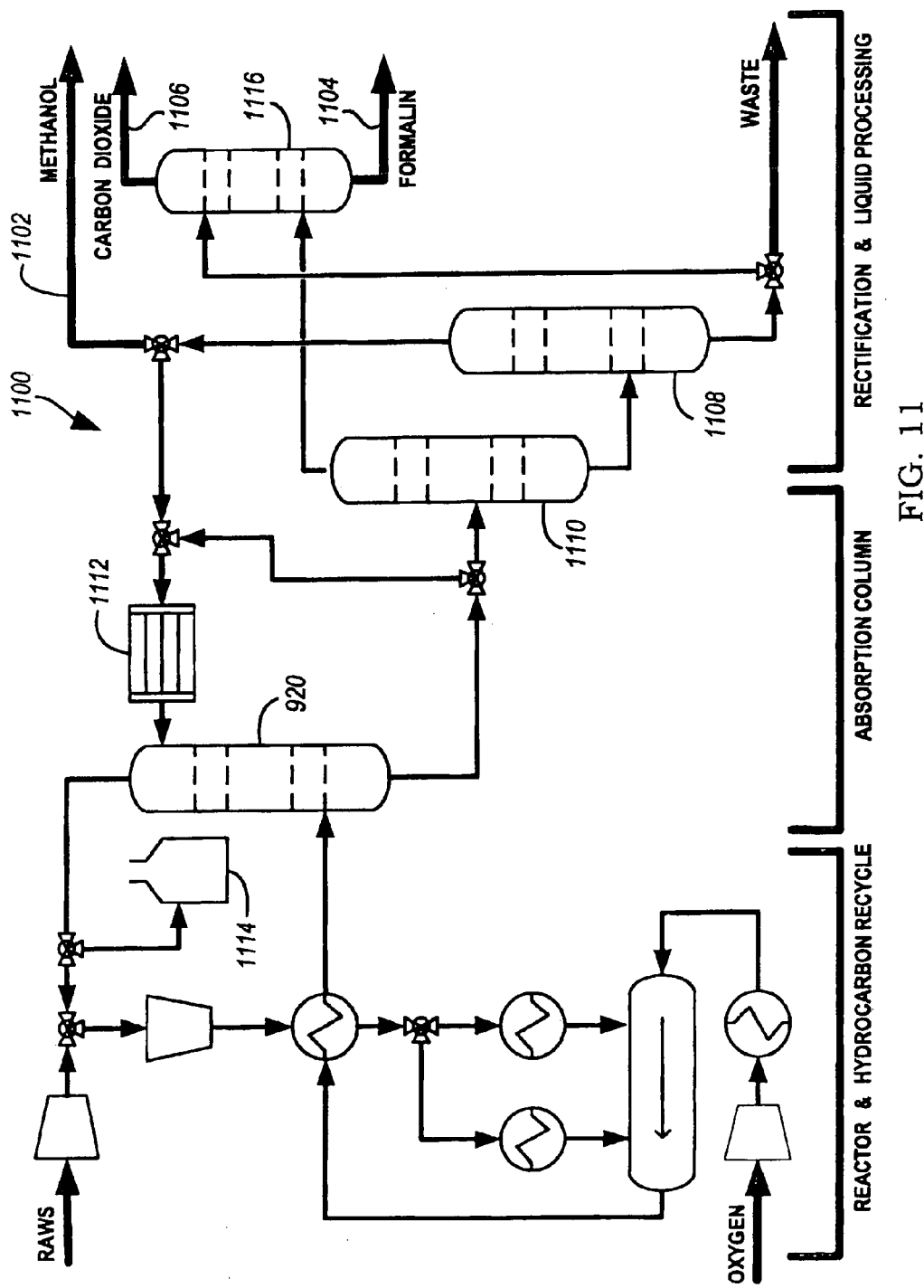
FIG. 11 represents yet another alternate $C_1$-$C_4$ alkane (e.g., without limitation, methane) to alkyl oxygenate (e.g., without limitation, methanol) plant according to the teachings of the present invention.

FIG. 11 presents process embodiment 1100 for generating a methanol product stream and formaldehyde with a front end process loop essentially similar to process 900 presented in FIG. 9, but incorporating an in-situ formaldehyde distillation system 1110 and methanol distillation system 1108 to generate methanol product stream 1102. The stream from methanol distillation system 1108 cools formaldehyde distillation system 1110 overheads to separate carbon dioxide (product stream 1106) and formaldehyde (product stream 1104) in absorber-blender 1116. A recycle stream of methanol to the scrubber is drawn from methanol distillation system 1108 and chilled in chiller 1112 to provide a high-efficiency scrubber for condensing the reactor product stream. Furnace or thermal oxidizer 1114 oxidizes a purge to remove non-reactive inerts (e.g., without limitation, nitrogen) with some alkane (methane) from the reactor-scrubber process loop and thereby augment efficient use of the reactor.

While a traditional tubular-flow reactor can be used with any of the above-described processes as either reactor 100 and/or reactor 914, preferred reactor embodiments are described in the discussion of FIGS. 12 to 24B.

Turning now to a deeper consideration of kinetics in the reaction and further embodiments for providing an improved reactor system for executing the overall reaction for the partial oxidation of natural gas to methanol, formaldehyde, and other oxygenates, several compact production facilities have been described in FIGS. 1-11 that are suitable for small, isolated natural gas sources (stranded gas). Novel reactor systems for these processes are also further described beginning with FIG. 12 and, more specifically, as overviewed in FIGS. 12 and 20. Beginning considerations in these reactor designs derive from the nature of the overall direct oxygenation reaction itself.

In overview, the method for reaction comprises passing a mixture of natural gas and oxidant through a heated, continuous flow reactor system under conditions to optimize the formation of methanol, and to manipulate the reactor temperature, total pressure, and fuel (e.g., without limitation, natural gas) to oxidant ratio to control the relative amounts of reaction products. The reaction is a partial oxidation of a $C_1$-$C_4$ fuel, such as natural gas, by an oxidant, oxygen, air, or other suitable oxygen-containing compound (preferably oxygen in air or, most preferably, oxygen). The mixture contains a substantial excess of fuel (e.g., without limitation, natural gas) to prevent complete combustion to undesired products such as carbon dioxide and water.

The reaction is an exothermic, branched chain reaction. Chain branching causes an acceleration of the reaction rate via quadratic growth of chain carriers. Reactions of this type are characterized by an induction period during which chain carrier concentrations build up to the point where a very rapid rise in reaction rate and temperature occurs. The very rapid rise in reaction rate is because of the quadratic growth rate of chain carriers, and the very rapid rise in temperature is because of the increase of the rate of heat generation that accompanies the reaction rate. Complete consumption of oxidant, the limiting reagent, occurs before the fuel (e.g., without limitation, natural gas) is entirely consumed, which limits the temperature rise. The ratio of oxidant to fuel (e.g., without limitation, natural gas) is arranged so that the selectivity for formation of methanol is optimized.

Reaction conditions favoring the best selectivity for methanol and other oxygenates are as follows. The composition of the reaction mixture, after combining the alkane-containing fed stream and the oxygen-containing feed stream, should be from about 1 mol % to about 10 mol % oxidant, preferably from about 2 mol % to about 5 mol % oxidant, and most preferably at about 2.5 mol % oxidant. The total pressure of the gases in the reactor system should be in the range of from about 6 MPa to about 10 MPa, preferably from about 7.5 MPa to about 9 MPa, and most preferably at about 8 Mpa. The reactor system wall temperature should be in the range of from about 600 K to about 900 K, and more preferably from about 723 K to about 823 K. The overall reactor residence time should be in the range of from about 1 second to about 40 seconds, more preferably from about 1 second to about 10 seconds, and most preferably from about 1 second to about 2.5 seconds.

At these conditions, methanol selectivity is in the range of from about 0.35 to at least 0.60 with lower selectivities for the other oxygenates of the alkane-containing feed stream. The conversion of methane is approximately 5 to 10%, and conversion of the other hydrocarbon components of the natural gas is comparable. After the reaction, separation and recycle of the unreacted hydrocarbons is performed.

For continuous operation, the fuel (e.g., a $C_1$-$C_4$ alkane or $C_1$-$C_4$ alkanes such as provided in natural gas) and oxidant must be well-mixed. For this purpose a mixing chamber/reactor is supplied for both thoroughly mixing the reaction components and for also inducing the generation of alkyl (e.g., without limitation, methyl) free radicals that are then contained in the output stream from the mixing chamber. In this regard, the mixing chamber therefore effectively provides an injectively-mixed backmixing reaction chamber ("backmix reaction chamber") in a reactor system having an injectively-mixed backmixing reaction chamber in fluid communication with a tubular-flow reactor for carrying out the overall reaction. While not falling ideally into either a classical continuously-stirred-tank reactor model or into a classical tubular-flow reactor model, the injectively-mixed backmixing reaction chamber of the embodiments has a number of aspects that indicate an operational character having more of a continuously stirred tank reactor or CSTR model affinity (further denoted as a continuous feed stirred tank reactor or CFSTR; and yet further denoted as a steady-state backmix flow reactor) than of a tubular or plug-flow reactor model affinity. The injectively-mixed backmixing reaction chamber has a space-time, respective to a combined feed rate of the alkane-containing feed stream and the oxygen-containing feed stream, of from about 0.05 seconds to about 1.5 seconds (a preferably contemplated space-time is about 0.1 seconds) so that the feeds can be effectively mixed and so that an initial induction period for generating alkyl free radicals (e.g., without limitation, methyl free radicals) can be accommodated before the injectively-mixed backmixing reaction chamber product stream (methane, oxygen, and methyl free radicals) is fed to the tubular-flow reactor for further reaction into methanol. In a preferred embodiment, the design of the injectively-mixed backmixing reaction chamber enables injective intermixing of the $C_1$-$C_4$ alkane and oxygen-containing feed streams to turbulently agitate streams together and to effectively turbulently agitate the injectively-mixed backmixing reaction chamber. In this regard, the generating of methyl free radicals is perceived to be the first kinetic step reaction in the set of kinetic step reactions that achieve direct oxygenation of methane to methanol (one respective alkyl oxygenate), and the use of an injectively-mixed backmixing reaction chamber prior to the tubular-flow reactor enables a degree of freedom for independent optimization of this methyl free radical induction step. Other free radicals derived from $C_2$-$C_4$ alkanes should usually have a shorter induction period than the methyl free radical under comparable conditions. The subsequent chain branching kinetic sub-reactions (kinetic sub-reaction steps) then covert the methyl free radicals and other components of the injectively-mixed backmixing reaction chamber product stream to methanol and other products; these later sub-reactions are best controlled in the tubular-flow reactor environment that has traditionally received the admixed (but unreacted) methane (alkane) and oxygen of prior systems.

The reactor system accordingly provides several degrees of freedom (e.g., without limitation, reactor space-time, temperature, and infective mixing as further subsequently discussed herein) for augmenting the initial kinetic series sub-reaction(s) and also for augmenting, with some independency from conditions augmenting the initial kinetic series sub-reaction(s), the subsequent kinetic series sub-reactions in the overall set of sub-reactions that combine to achieve the overall direct oxidation reaction of at least one $C_1$-$C_4$ alkane into at least one respective alkyl oxygenate.

With respect to methane in the alkane-containing feed stream, the induction of methyl free radicals in the mixing chamber/reactor (the injectively-mixed backmixing reaction chamber) is a clear departure from the prior teachings of documents such as U.S. Pat. No. 4,982,023 and U.S. Pat. No. 4,618,732, both of which, as noted in the Background, indicate that the feed streams are to be only mixed prior to their introduction into a reactor.

The reactants are fed to the mixing chamber/reactor (the injectively-mixed backmixing reaction chamber) in separate streams. Upon emergence from the injectively-mixed backmixing reaction chamber, the reactants are then fed to the tubular-flow reactor. The mixing must be done thoroughly, with the goal of attaining a uniform or essentially uniform distribution of reactant concentration in the injectively-mixed backmixing reaction chamber product stream. This is necessary to avoid oxidation of the desired products—methanol and other oxygenates. Such oxidation otherwise occurs in incompletely mixed regions where relatively high oxidant concentrations exist, with commensurate reduction of product yield. In this regard, the mixing time in the injectively-mixed backmixing reaction chamber must be relatively brief compared to the residence time in the tubular-flow reactor. In view of the overall preferred residence times for the reactor system as whole, from about 1 second to about 2.5 seconds, the residence time in the injectively-mixed backmixing reaction chamber must be at least 0.1 second. In this regard, actual turbulent intermixing of gases can be achieved in as little as 1 ms. While there are several embodiments for achieving satisfactory mixing, as will be hereinafter described, a preferred embodiment for use with the shortest residence times uses essentially opposed turbulent jets with a diverter diffuser cone having its apex-tending side (apexial end) closest to the tubular-flow reactor. The purpose of the cone is to minimize long residence times for sub-portions of the contents of the injectively-mixed backmixing reaction chamber in view of the high reactivity of the alkyl (e.g., methyl) free radicals.

The reactor walls must be inert in the chemical environment of the reaction. The reactor construction material must be steel, preferably stainless steel, to contain the necessary total pressure. Insofar as a steel surface diminishes methanol selectivity, the steel is preferably coated with an inert coating, such as Teflon™, or an organic wax. Insertion of a Pyrex™ or quartz sleeve into the reactor also provides a relatively inert surface.

A flow restriction baffle is positioned in the injectively-mixed backmixing reaction chamber output to augment pressure drop between the injectively-mixed backmixing reaction chamber and the tubular-flow reactor and thereby achieve a desired residence time fine turning feature (degree of freedom of control) in the injectively-mixed backmixing reaction chamber. In a preferred embodiment, the flow restriction baffle (bulkhead with apertures for enabling a fluid passageway) is conveniently axially movable so that alternative baffle positions can be deployed in custom-configuring the effective space-time in the injectively-mixed backmixing reaction chamber prior to a process run instance or during a process run. In a preferred embodiment, the flow restriction baffle is further in close proximity to a blocking component that is conveniently axially movable so that variable baffle (bulkhead) passageways can be defined by partially blocking the apertures in the baffle (bulkhead) in custom-configuring the effective space-time in the injectively-mixed backmixing reaction chamber prior to a process run instance or during a process run; this feature provides another degree of freedom for operational control.

Turning now to an overview of the tubular-flow reactor, the axial position of the temperature maximum is quite sensitive to the reactor inlet temperature, total flow rate, and reactant composition. Fluctuations in any of these quantities can cause the position of the reactor "hot spot" to move. In an extreme case, the "hot spot" can move out of the reaction vessel and thereby adversely affect performance. The tubular-flow reactor is therefore preferably equipped in one embodiment with a thermocouple that can be translated axially (along the axis of general flow in the reactor) via a sliding seal. In another embodiment, a plurality of thermocouples disposed to measure the tubular-flow reactor temperature profile along the axis of flow enable temperature monitoring. The thermocouple set monitors the axial gas phase temperature distribution in the reactor, and the thermocouple measurements are also used for control of the reactor.

The methanol, formaldehyde and other oxygenates can undergo thermal decomposition in the high temperatures of the tubular-flow reactor, resulting in product loss. Such decomposition is minimized by cooling of the reactor contents at a location immediately downstream from the "hot spot". Because wall cooling is not sufficiently responsive, a preferred embodiment employs injection of a cold gas by means of a tube whose axial position can also be changed by means of a sliding seal. The cold gas is preferably natural gas, but carbon dioxide, nitrogen, or another inert substance may also be used.

Figure 12:
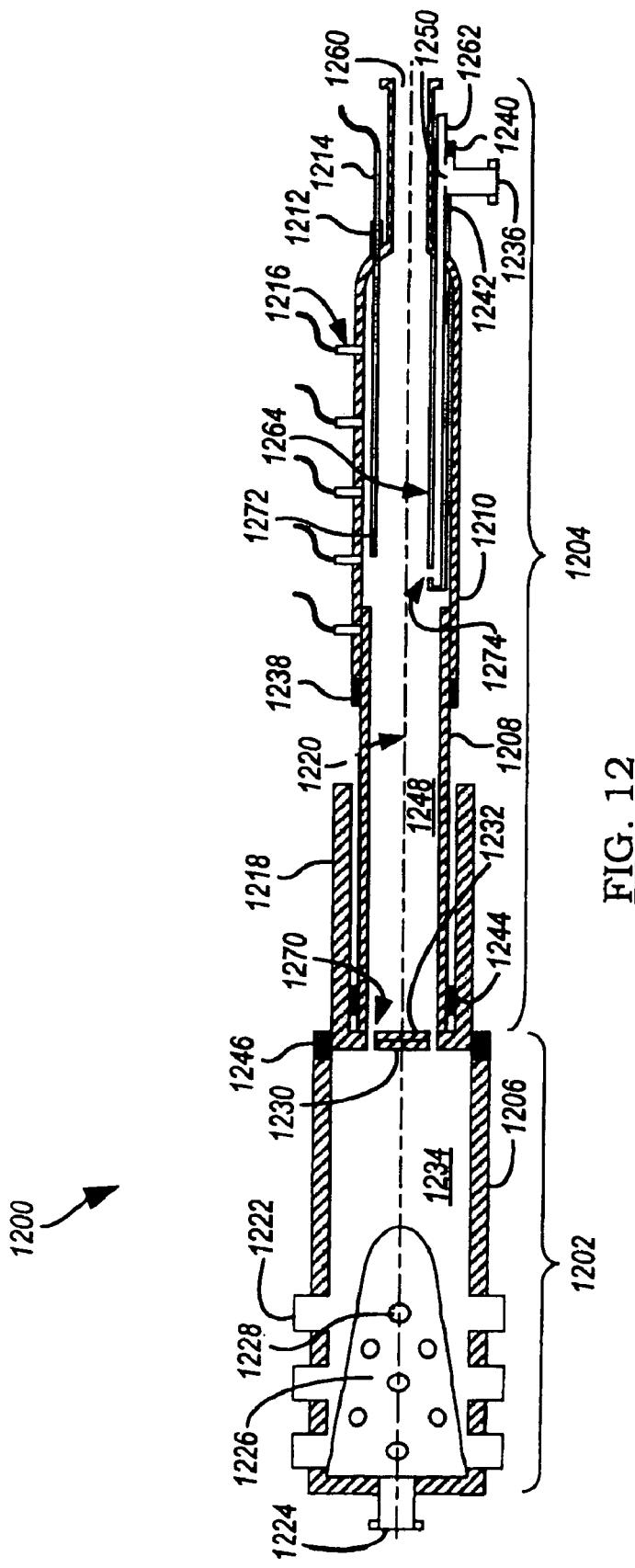
FIG. 12 presents a cross section simplified view of one embodiment of a reactor system having an injectively-mixed backmixing reaction chamber in close coupling to a tubular-flow reactor.

FIG. 12 presents a cross section simplified view 1200 of a reactor system having an injectively-mixed backmixing reaction chamber 1202 in close coupling to a tubular-flow reactor 1204 so that a reactor system having an injectively-mixed backmixing reaction chamber in fluid communication with a tubular-flow reactor is provided for one of the processes described in conjunction with FIGS. 1-11. The main chamber and reactor sections of the reactor system are aligned along axis 1220 with the injectively-mixed backmixing reaction chamber having housing 1206 (defining internal volume 1234 with a cylindrical surface in co-operation with bulkhead 1232). Tubular-flow reactor 1204 has housing 1210 defining internal volume 1248 in co-operation with slideable tubular-flow reactor 1204 section having housing 1208 and with bulkhead 1232. An alkane-containing gas feed stream (a first fluid stream) enters through alkane gas input 1222 and similar alkane gas inputs as depicted. An oxygen-containing gas feed stream (a second fluid stream) enters through oxygen gas input 1224 and conical diverter/distributor 1226. Conical diverter/distributor 1226 has a conical base (base 1614 of FIG. 16) connected to a portion of housing 1206 in opposite disposition to bulkhead 1232. A backmixing reaction chamber output is established by bulkhead (baffle) 1232 and passageway 1270 (with its associated fluid passageways shown in more detail in FIGS. 17A and 17B) and optional blocking component 1230. Bulkhead (baffle) 1232 and optional (for variable passageway definition in real-time operation of the reactor system) blocking component 1230 provide passageways such as passageway 1270 for feeding the injectively-mixed backmixing reaction chamber 1202 product stream to tubular-flow reactor 1204. Tubular-flow reactor 1204 therefore has a tubular-flow reactor input in fluid communication through passageway 1270 with the backmixing reaction chamber 1202 output at bulkhead (baffle) 1232 and blocking component 1230. Alkane gas input 1222 (along with similar alkane gas inputs as depicted) and oxygen gas input 1224 with conical diverter/distributor 1226 and oxygen input aperture 1228 (along with similar alkane gas inputs as depicted) are configured (positioned and sized with respect to the flows of the alkane-containing and the oxygen-containing feed streams) to turbulently agitate reaction components within internal volume 1234 of injectively-mixed backmixing reaction chamber 1202 by injective intermixing of the alkane-containing gas feed stream and the oxygen-containing gas feed stream.

Tubular-flow reactor 1204 has a tubular-flow reactor output 1260, and tubular-flow reactor 1204 has cooling gas input 1274 disposed between the tubular-flow reactor input from passageways (passageway 1270) at bulkhead 1232 and tubular-flow reactor output 1260 for receiving a cooling gas stream (that enters at cooling input port 1236 and then into cooling gas internal input port 1250 before proceeding to cooling gas input 1274) and thereby quenchably cooling tubular-flow reactor 1204. In this regard, cooling gas input 1274 in one embodiment is in an elongated tube (tube 1262) with at least one aperture 1274 (see FIGS. 18A and 18B for cross-sectional detail respective to axis 1220) for conveying the cooling quench flow into reactor space 1248. Tube 1262 co-operates with guide tube 1264. In one embodiment, tube 1262 rotates within guide tube 1264 to regulate the amount of quench delivered to a location. In an alternative embodiment, tube 1262 is axially slideable (with reference to axis 1220) to position within tubular-flow reactor 1204 and provide local quenching. In yet another embodiment, tube 1262 rotates within guide tube 1264 to regulate the amount of quench delivered to a location and also is axially slideable (with reference to axis 1220) to position within tubular-flow reactor 1204 and provide local quenching. The quenching components (including drawing references 1262, 1250, 1236, 1264, and 1274) therefore provide a degree of freedom for managing the temperature profile along axis 1220 within tubular-flow reactor 1204. Thermocouples such as thermocouple 1216 and similar thermocouples as depicted provide measurements for the temperature profile in one embodiment. A sliding thermocouple 1214 (with thermocouple sensor 1272 and sealed with sliding seal 1212 to housing 1210) provides measurements for the temperature profile in another embodiment. FIG. 12 shows an embodiment having stationary thermocouples such as thermocouple 1216 was well as a sliding thermocouple 1214 (with thermocouple head 1272).

Tubular-flow reactor 1204 has housing 1210 defining internal volume 1248 in co-operation with the slideable tubular-flow reactor 1204 section having housing 1208 and also having bulkhead 1232 (with optional blocking component 1230 for providing passageway 1270 as a cross-sectionally-variable passageway). Bulkhead 1232 and blocking component 1230 are in slideably-sealed interface to backmixing reaction chamber housing 1206 and are therefore both effectively attached to the slideable tubular-flow reactor 1204 section having housing 1208. Housing section 1208 is therefore in slideably-sealed interface to housing 1210 and also to housing 1206 with seals 1244, 1246, and 1238 providing isolation from the external environment. Injectively-mixed backmixing reaction chamber 1202 has an injectively-mixed backmixing reaction chamber internal volume 1234 defined by backmixing reaction chamber housing 1206 and by bulkhead 1232 (with optional blocking component 1230). Bulkhead 1232 (and blocking component 1230) is therefore slideably movable during real-time operation of the reactor system of view 1200 to progress within backmixing reaction chamber housing 1206 toward input 1224 to thereby commensurately diminish internal volume 1234, and bulkhead 1232 (and blocking component 1230) is alternatively slideably movable during real-time operation to retract away from input 1224 to thereby commensurately expand internal volume 1234. In the embodiment of FIG. 12, tubular-flow reactor 1204 has a tubular-flow reactor internal volume 1248 defined by tubular-flow reactor housings 1208 and 1210 and by bulkhead 1232 (with blocking component 1230). Bulkhead 1232 (and blocking component 1230) is therefore slideably movable during real-time operation of the reactor system of view 1200 to thereby commensurately diminish internal volume 1248 when moving away from toward input 1224, and bulkhead 1232 (with optional blocking component 1230) is alternatively slideably movable during real-time operation to move toward input 1224 to thereby commensurately expand internal volume 1248. This moveable interface enables a degree of freedom for managing relative space-time (essentially equivalent, for gaseous flow, to internal reaction volume divided by volumetric flow rate moving through that internal reaction volume) within the reactor system of view 1200 between both tubular-flow reactor 1204 and injectively-mixed backmixing reaction chamber 1202.

Essentially, the functionality enabled by the features of bulkhead 1232 (and blocking component 1230) is for a backmixing reaction chamber where the internal volume (defined by an internal surface of a housing and also by the surface of any component in moveably sealed interface to that internal surface) can be readily modified so that the space-time, provided by the backmixing reaction chamber to chemically reacting compositional components in gaseous fluids flowing within the internal volume, can be modified without necessarily modifying flow rate(s), turbulency, and/or pressure drop of those fluids. In this regard, any approach for modifying the internal volume from a first internal volume to a second internal volume is potentially useful. In one conceptualized embodiment, for instance, bulkhead 1232 is axially fixed, conical diverter/distributor 1226 has a base wide enough to slideably seal against backmixing reaction chamber housing 1206, conical diverter/distributor 1226 has a slideable tube (not shown) interconnecting to input 1224, and conical diverter/distributor 1226 thereby commensurately diminishes internal volume 1234 when moving away from input 1224 and commensurately expandes internal volume 1234 when moving toward input 1224. In another conceptualized embodiment, housing 1206 has a movable portion that invades into the chamber to diminish internal volume 1234 and alternatively withdraws from the chamber to increase internal volume 1234. In yet another conceptualized embodiment, an internal diaphramed component modifies its characteristics to commensurately modify internal volume 1234.

Seal 1246, seal 1212, seal 1244, seal 1238, seal 1242, and seal 1240 all enable slideable movement of the movable components of the reactor system of view 1200. Rotation component 1218 enables rotation of blocking component 1230 during operation. As should be apparent, movement of components (especially during operation of the reactor system of view 1200) is preferably achieved with assistance from variable speed motors, levers, levers with associated gearing, and/or step-motors and with associated gearing (not shown but that should be apparent to those of skill).

In operation, an alkane-containing feed stream and an oxygen-containing feed stream are input to injectively-mixed backmixing reaction chamber 1202 through input ports such as input 1222 (alkane-containing feed stream) and input 1224 (oxygen-containing feed stream). Injectively-mixed backmixing reaction chamber 1202 internal conditions are managed to induce alkyl free radical formation in injectively-mixed backmixing reaction chamber 1202 to yield an injectively-mixed backmixing reaction chamber product stream for output and fluid communication into tubular-flow reactor 1204 through passageways such as passageway 1270 in bulkhead 1232 and blocking component 1230. The components are sized and arranged to provide significant molecular momentum in the entering fluids so that injective mixing and a turbulent reaction fluid in injectively-mixed backmixing reaction chamber 1202 are established. The injectively-mixed backmixing reaction chamber product stream feed to tubular-flow reactor 1204 via passageway 1270 therefore comprises oxygen, unreacted alkane, and at least a portion of the alkyl free radicals that were induced in injectively-mixed backmixing reaction chamber 1202. In this regard, the "reaction" of alkane to alkyl oxygenate (focally, the "reaction" of methane to methanol) involves a large plurality of reactions (termed herein also as kinetic series sub-reactions or kinetic sub-reactions); indeed, there may be at least 60 kinetic series sub-reactions in the overall "reaction" of methane to methanol and other alkyl oxygenates occurring in the system. The initial kinetic series sub-reaction occurs to induce an alkyl radical from an alkane when an alkane molecule is exposed to molecular oxygen. There is therefore efficacy in handling this reaction in a separated injectively-mixed backmixing reaction chamber that is in fluid communication with a tubular-flow reactor where a consistent (with time and at steady state operation) portion of the alkyl radicals will be essentially conveyed (fed into the tubular-flow reactor) to provide the basis for enabling the many subsequent parallel and sequential kinetic series sub-reactions that require a heat management approach more amenable to tubular-flow reactors than to injectively-mixed backmixing reaction chambers. Although close-coupled to a tubular-flow reactor in the embodiments, the injectively-mixed backmixing reaction chamber provides the reaction components with an essentially universal compositional and physical (temperature, pressure, and molecular momentum) operational state within its space-time compared to a tubular-flow system; this enables management of the critical alkyl radical induction step independently from the tubular-flow reactor where, along the axis of the tubular-flow reactor, the reaction components have an axially (and probably radially) differentiated composition and physical state.

As should be apparent to those of skill, the management of scale-up in such a system as the reactor system of view 1200 needs to manage the challenge of providing acceptable molecular momentum in increasing space-time situations; if the molecular momentum diminishes, the reaction fluid in the injectively-mixed backmixing reaction chamber will migrate toward the laminar flow range and the overall necessary consistency of the injectively-mixed backmixing reaction chamber reaction fluid may thereby become potentially compromised; therefore, a reactor according to view 1200 appears efficacious in small-scale processing for making "stranded gas" a valuable commodity.

The overall reactor system space-time, respective to a combined feed rate of the alkane-containing feed stream and the oxygen-containing feed stream, is not greater than 40 seconds, and is preferably not greater than 2.5 seconds. Reaction space-time for the injectively-mixed backmixing reaction chamber is managed to be not greater than 1.5 seconds.

FIGS. 13A and 13B presents cross section simplified views 1300 and 1350 of details in modifying the internal volume of the injectively-mixed backmixing reaction chamber 1202 of FIG. 12. In this regard, an alternative view 1300 is presented for injectively-mixed backmixing reaction chamber 1202 in FIG. 13A where a "hairbrush" distributor 1308 (further detailed in FIGS. 15A and 15B) for the oxygen-containing feed stream is depicted. View 1300 of FIG. 13A generally shows a bulkhead 1304 and optional blocking component 1302 in fully expanded or extended orientation to housing 1306.

Reactor view 1350 of FIG. 13B generally shows bulkhead 1304 and optional blocking component 1302 in inserted orientation to housing 1306 to diminish the volume (and, in steady state operation, the space time) of the injectively-mixed backmixing reaction chamber respective to the volume (space-time) of view 1300.

Figure 14A:
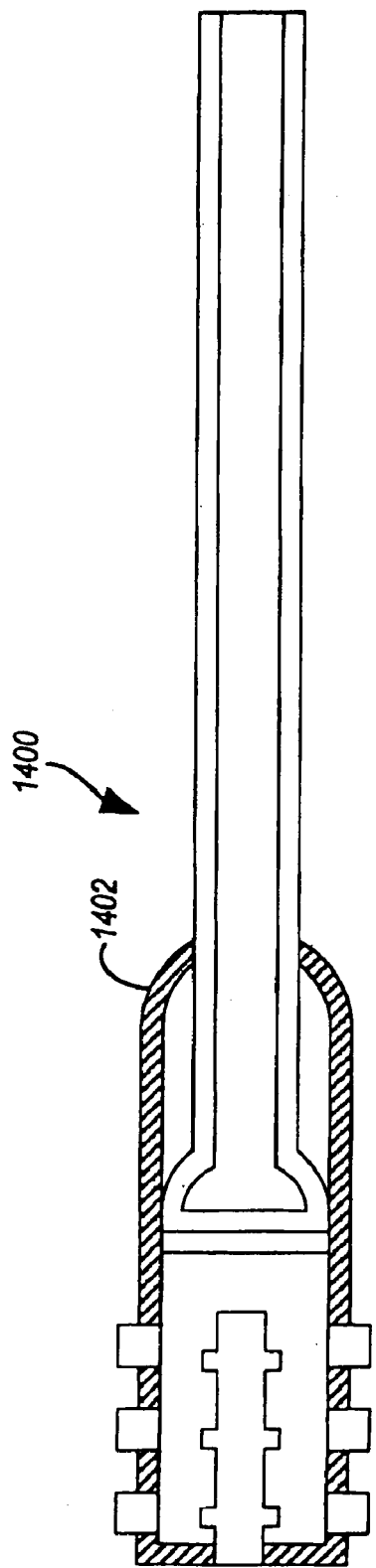
FIG. 14A presents a cross section simplified view of an alternative design for the injectively-mixed backmixing reaction chamber of FIG. 12.

FIG. 14A presents a cross section simplified view 1400 of another alternative design for injectively-mixed backmixing reaction chamber 1202 of FIG. 12. In this regard, a hemispherical head portion 1402 is profiled for the housing, with a comparably hemispherical profile in the inserted bulkhead.

Figure 14B:
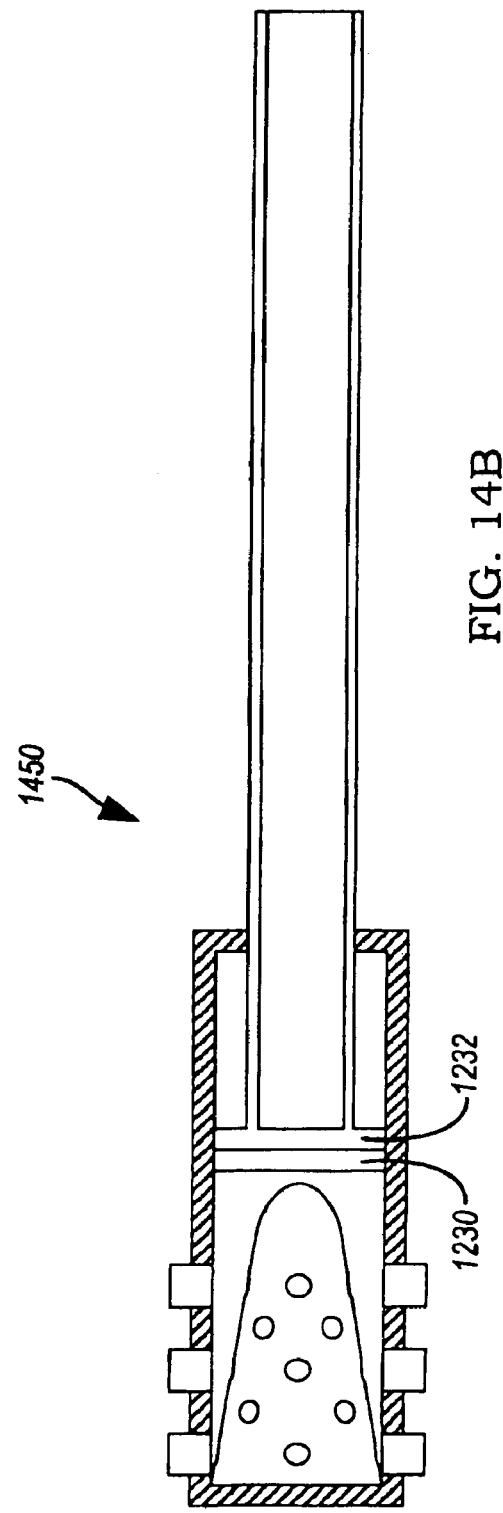
FIG. 14B shows a view of the injectively-mixed backmixing reaction chamber of FIG. 12 with a modified internal volume from that shown in FIG. 12.

FIG. 14B shows a view 1450 depicting the injectively-mixed backmixing reaction chamber 1202 of FIG. 12 with a modified internal volume from that shown in FIG. 12. Bulkhead 1232 and (optional) blocking component 1230 are depicted in inserted orientation to housing 1206 to diminish the volume (and, in steady state operation, the space time) of the injectively-mixed backmixing reaction chamber 1202 respective to the volume (space-time) of view 1200.

FIGS. 15A and 15B present aligned cross-sectional views 1500 and 1550 of the "hairbrush" fluid delivery insert 1308 for an alternative design for injectively-mixed backmixing reaction chamber 1202 of FIG. 12. Axis 1504 is aligned with axis 1220 in the preferred embodiment, with view 1500 showing "hairbrush" distributor 1308 detail respective to a plane perpendicular to axis 1504, and view 1550 showing "hairbrush" distributor 1308 detail respective to a plane parallel to axis 1504. The oxygen-containing feed stream is input into internal flow space 1234 from a plurality of apertures (such as aperture 1502) disposed along the injectively-mixed backmixing reaction chamber axis in the essential centerline of the cylindrical surface of housing 1206 and in non-parallel orientation to the injectively-mixed backmixing reaction chamber axis 1220 when axis 1504 is essentially aligned with axis 1220.

FIG. 16 presents a cross section simplified view 1600 of internals for conical fluid delivery insert 1226 for delivering the oxygen-containing feed stream into the injectively-mixed backmixing reaction chamber 1202 of FIG. 12. The internal flow diverter is defined by a conical surface 1604 having an axis 1602. A conical base 1614 is at one end of axis 1602, and apexial end 1612 (an end that, if the cone were extended, would ultimately converge to provide the apex of the cone) is at the other end of axis 1602. As shown in view 1200 of FIG. 12, axis 1602 is aligned with axis 1220 of injectively-mixed backmixing reaction chamber 1202 when conical diverter 1226 is disposed within cylindrical housing 1206 such that the backmixing reaction chamber output (passageway 1270) is more proximate to apexial end 1612 than to conical base 1614. The oxygen-containing feed stream is input into inlet 1610 (from inlet 1224 of FIG. 12) and then into internal flow space 1234 from a plurality of apertures 1608 disposed along injectively-mixed backmixing reaction chamber axis 1220 (axis 1602) and in non-parallel orientation to axis 1220. Internal passageway 1606 fluidly conveys the oxygen-containing feed stream to the plurality of apertures 1608.

Figure 17A:
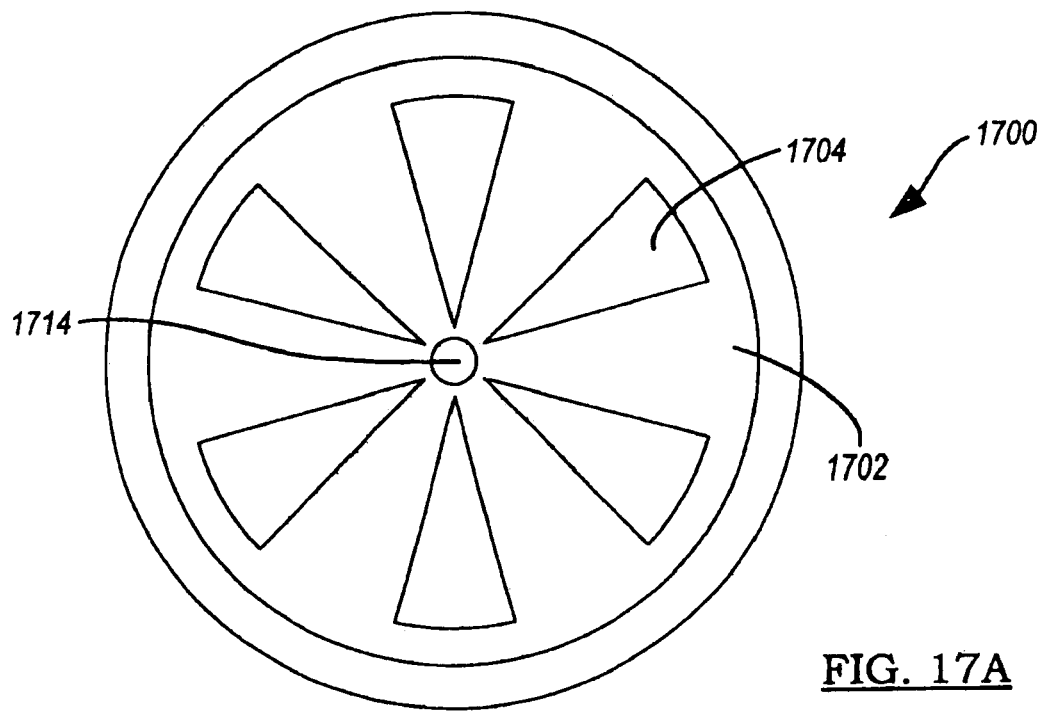
FIGS. 17A and 17B present a cross section simplified view of baffle details and positioning at the interface between the injectively-mixed backmixing reaction chamber and the tubular-flow reactor of the reactor system embodiments of FIGS. 12 and 20.
Figure 17B:
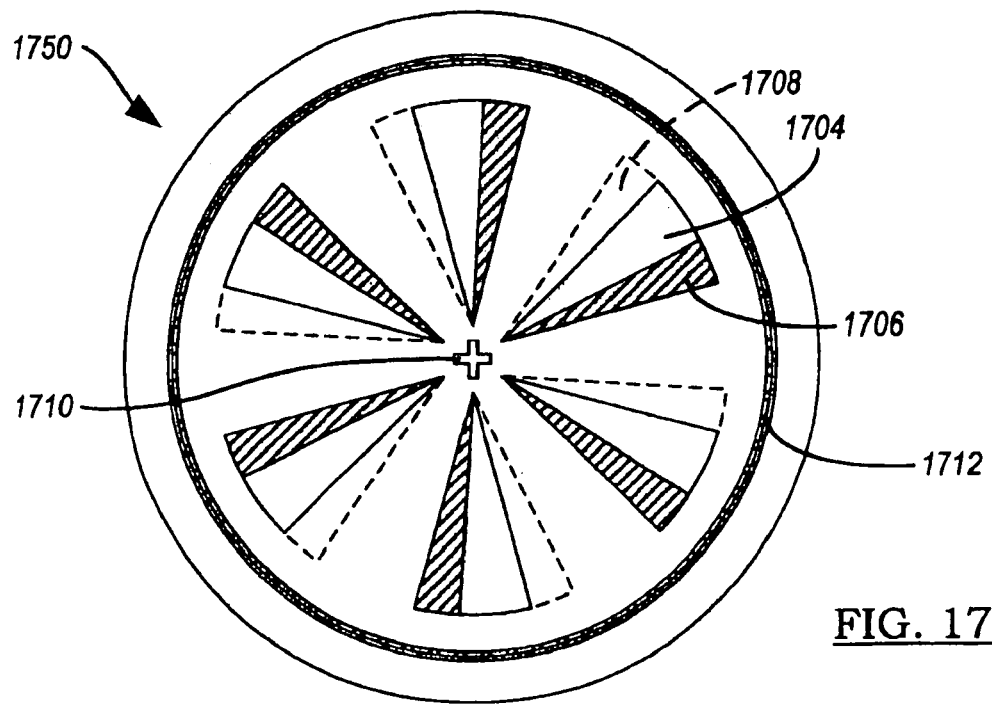

FIGS. 17A and 17B present cross section simplified views of the interface baffle (1232/1230) details and positioning at the interface between injectively-mixed backmixing reaction chamber 1202 and tubular-flow reactor 1204 of the FIG. 12 reactor system. In view 1700 of FIG. 17A, bulkhead 1702 has at least one aperture 1704 defining a passageway (see passageway 1270 in FIG. 12) for fluid communication of an injectively-mixed backmixing reaction chamber product stream from injectively-mixed backmixing reaction chamber 1202 into tubular-flow reactor 1204. Bulkhead 1702 (bulkhead 1232 in FIG. 12) provides the passageway with at least one aperture 1704 having a cross-sectional area. In a flowing fluid, bulkhead 1702 with apertures 1704 defines a baffle for creating a pressure drop between injectively-mixed backmixing reaction chamber 1202 and tubular-flow reactor 1204 as the flowing fluid passes from injectively-mixed backmixing reaction chamber 1202 into tubular-flow reactor 1204. In a "tuned" reactor system, apertures 1704 can be precisely sized in one embodiment so that no blocking component is needed; such an arrangement has fewer degrees of freedom for operation, but also is less complex from a sealing and construction standpoint. For real-time operational varying of the effective passageway created by aperture 1704, a blocking component 1230 is deployed in an alternative embodiment where, as shown in view 1750 of FIG. 17B, blocking component 1230 can be rotated to "block" a portion of the cross-sectional area of aperture 1704 where a portion of blocking component 1706 (blocking component 1230 of FIG. 12) is shown constricting the passageway of aperture 1704 (note that view 1750 can be conceptualized as a view parallel to axis 1220 and toward injectively-mixed backmixing reaction chamber 1202 from tubular-flow reactor 1204) and thereby restricting the passageway.

In a preferred embodiment, bulkhead (1232/1702) has at least one aperture 1704 as a first aperture, and blocking component (1230/1706) has at least one second aperture (1708). These first and second apertures preferably have essentially identical dimensions, and first aperture 1704 and second aperture 1708 are mutually disposed to positionally align, in one relative positioning of bulkhead (1232/1702) and blocking component (1230/1706), to define the passageway (1270) to have a cross-sectional area essentially equivalent to the cross-sectional area of the first aperture. In view 1750, this can be appreciated by considering that the portion of aperture 1704 that is not blocked from passageway use by blocking component 1706 is also the portion of aperture 1708 that is not blocked from passageway use by bulkhead 1702.

Figure 21:
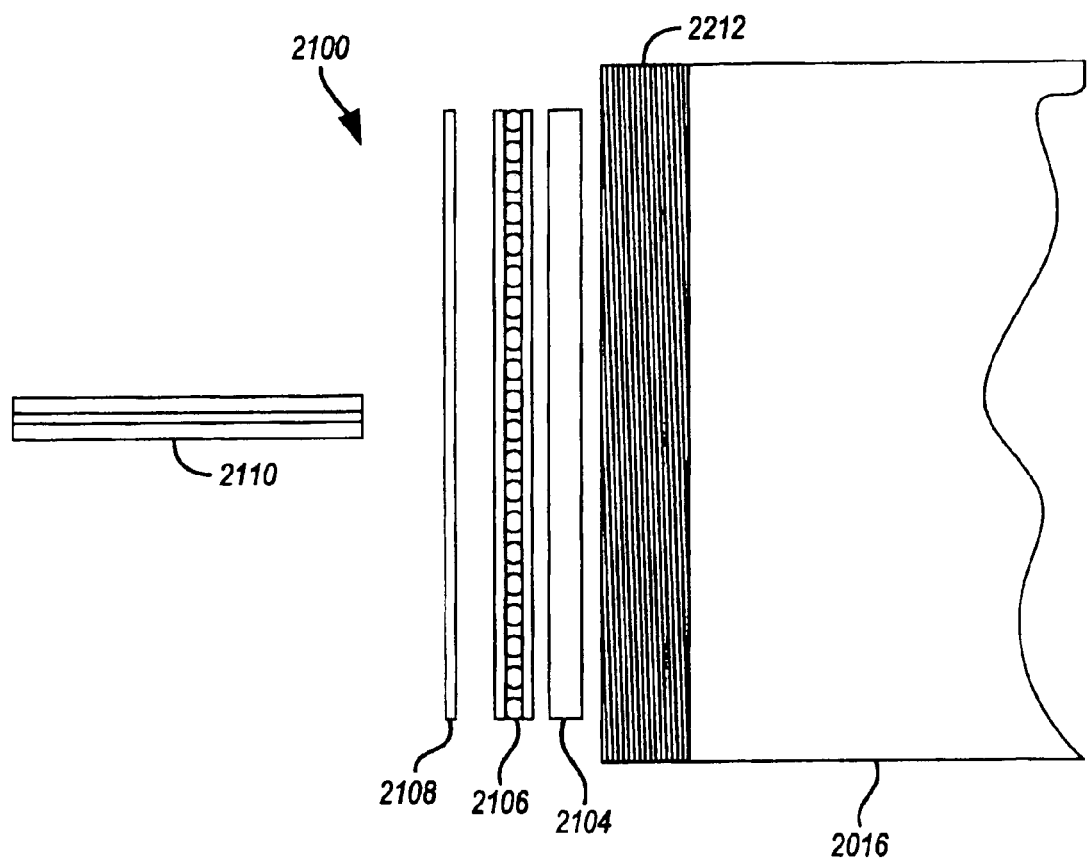
FIG. 21 presents bulkhead/baffle details for an embodiment of the interface between the injectively-mixed backmixing reaction chamber and the tubular-flow reactor of the reactor system embodiments of FIGS. 12 and 20.

An alternative embodiment of the combination of bulkhead (1232/1702) and blocking component (1230/1706) that does not include use of rotation component 1218 is further discussed with respect to FIG. 21. In this alternative embodiment, bulkhead (1232/1702) is movable respective to stationary blocking component (1230/1706) where key slot 1710 provides an axially (with respect to axis 1220) slideable restraint against key 2110 (FIG. 21) for prohibiting rotation of blocking component (1230/1706). In this embodiment, bulkhead (1232/1702) is firmly attached to housing 1208, but housing 1208 further rotates about axis 1220 to achieve a variable passageway 1270 defined by aperture 1704 and aperture 1708. Key 2110 is affixed to housing 1206 (details not shown), and aperture 1714 (FIG. 17A) provides a non-resistive opening for key 2110 to pass into internal volume 1248 so that bulkhead (1232/1702) and blocking component (1230/1706) move axially (axis 1220) respective to inlet 1224 with blocking component 1230/1706 always restrained and bulkhead 1232/1702 always capable of rotation about axis 1220.

Ball bearings 1712 are used in preferred embodiments to augment smooth rotation of the movable component (either of bulkhead 1232/1702 or blocking component 1230/1706 depending upon their particular embodiment) against the non-movable component in the baffle system.

FIGS. 18A and 18B present cross sectional simplified views 1800, 1850, and 1860 of details and positioning for the variable position quenching inlet 1274 for the FIG. 12 reactor system. Guide tube 1264 is shown in perpendicular cross-sectional in view 1800 respective to axis 1220 as tube cross-section 1802 having an elongated slot 1808 running along axis 1220. The elongated slot is difficult to show in FIG. 12, but it is depicted in FIGS. 18A and 18B as fully open passageway 1808 to convey the axial slot; quench tube 1804/1262 is shown with aperture 1806/1274—see inlet passageway 1274 in FIG. 12—to show that it is an opening having substantially less axial dimension than the axial dimension of slot 1808 of guide tube 1802/1264. Tube 1804/1262 co-operates with guide tube 1802/1264 as shown in view 1850 to not convey quench into internal volume 1248 when aperture 1806 is rotated to block the passageway (1274) with the internal surface of guide tube 1802/1264. In one embodiment, tube 1804/1262 is axially slideable within guide tube 1802/1264 to reposition aperture 1806/1274 axially along axis 1220. View 1860 then shows rotation of radial alignment between tube 1804/1262 and guide tube 1802/1264 so that passageway/inlet 1274 is enabled. Note that several alternative sets (not shown) of apertures 1806 can be readily provided at different radial positions of tube 1804 to provide alternative quench patterns as a function of the radial orientation of tube 1804/1262 along axis 1220 in tubular-flow reactor 1204.

FIGS. 19A and 19B present a series of temperature profiles for the tubular-flow reactor of the FIG. 12 reactor system in operation. In this regard, axis of abscissas 1904 and axis of ordinates 1906 are identical throughout FIGS. 19A and 19B, with axis of abscissas 1904 showing distance along axis 1220 of tubular-flow reactor 1204 and axis of ordinates 1906 depicting temperature within the reaction fluid of tubular-flow reactor 1204. Locus 1902 (FIG. 19A) is a conceptualized depiction of a temperature profile for tubular-flow reactor 1204 without benefit of quenching. Locus 1922 (FIG. 19B) is a conceptualized depiction of a temperature profile for tubular-flow reactor 1204 with benefit of quenching at location 1938. The afore-discussed kinetic series sub-reactions will vary in their activity depending upon the temperature profile along axis 1220 within tubular-flow reactor 1204. So, for instance, the product mix from tubular-flow reactor 1204 will be different for each of Loci 1902, 1922, and 1932 per their differentiated thermal profiles, commensurately differentiated energies, and commensurately differentiated kinetic activity for individual sub-reactions in the kinetic series sub-reaction set. The quenching tube design therefore affords yet another degree of freedom for optimizing the composition of an alkyl oxygenate reactor system product stream generated from a $C_1$-$C_4$ alkane-containing feed stream and an oxygen-containing feed stream.

Figure 20:
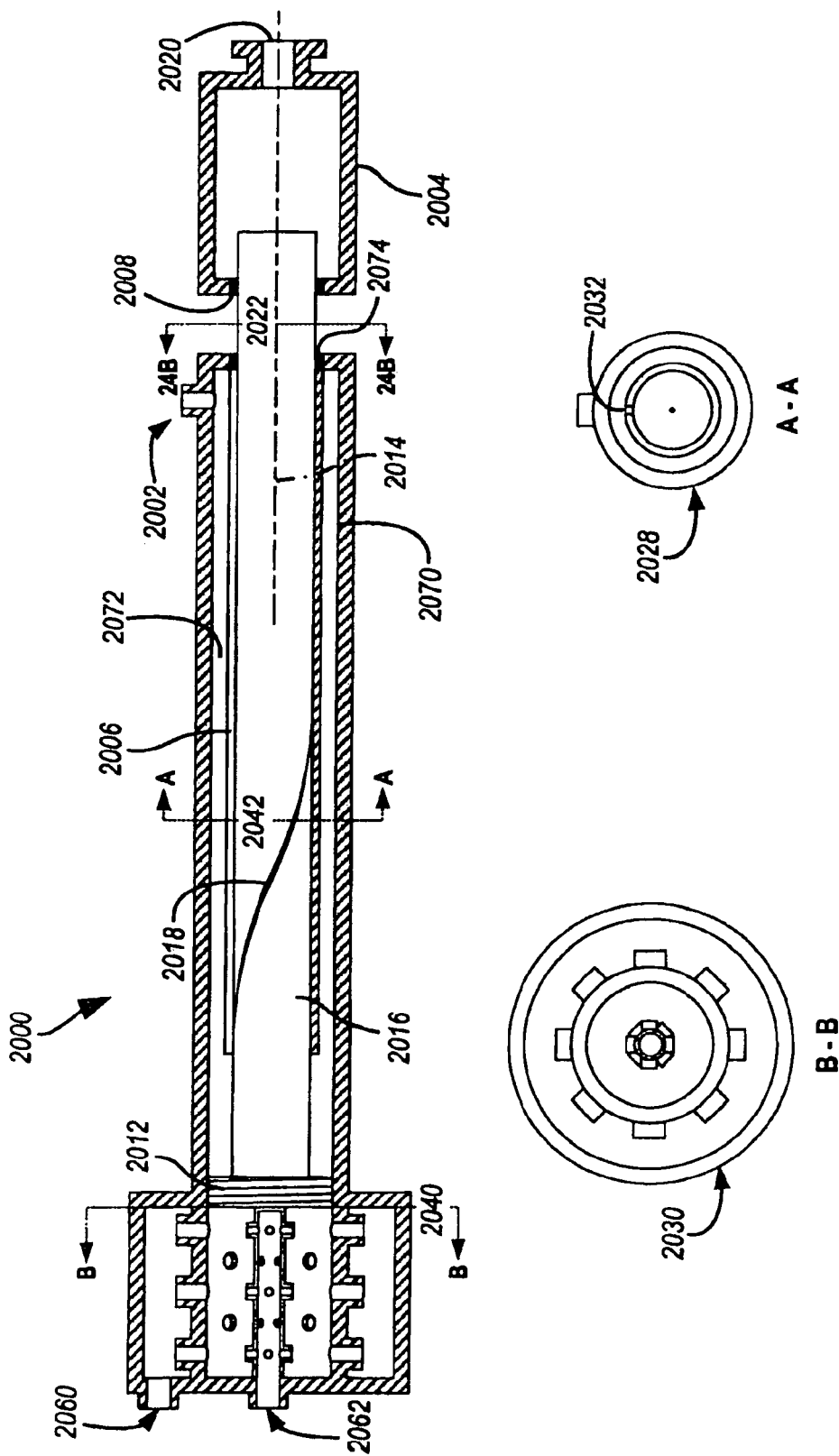
FIG. 20 presents a cross section simplified view of an alternative embodiment of a reactor system having an injectively-mixed backmixing reaction chamber in close coupling to a tubular-flow reactor.

FIG. 20 presents a cross section simplified view 2000 of an alternative embodiment of a reactor system having an injectively-mixed backmixing reaction chamber in close coupling to a tubular-flow reactor. The interface baffle assembly (bulkhead 1232 and blocking component 1230 assembly embodiments as described with respect to FIG. 12 and the alternative key-restrained deployment embodiments of FIGS. 17A, 17B, and 21) is slideably movable and rotated during real-time operation of the reactor system of view 2000 to progress and/or retract away from input 2062 by use of a threaded seal and connection facilitated by male threading 2012 (male threading 2212 in FIGS. 21 and 22A-22C). The majority of the injectively-mixed backmixing reaction chamber and the tubular-flow reactor share housing 2070, that is further threaded to provide female threading for co-operating with threading 2012/2212. FIGS. 22A-22C show further detail in this regard where FIG. 22A shows tubular-flow reactor sleeve 2016 in fully progressed position, FIG. 22B shows tubular-flow reactor sleeve 2016 in mid-point progression/retraction position, and FIG. 22C shows tubular-flow reactor sleeve 2016 in fully retracted position.

The backmixing reaction chamber and tubular-flow reactor of the reactor system of view 2000 are aligned along axis 2014. An alkane-containing gas feed stream (a first fluid stream) enters through alkane gas input 2060 and the plurality of alkane gas input apertures as depicted. An oxygen-containing gas feed stream (a second fluid stream) enters through oxygen gas input 2062 and the hairbrush distributor as previously discussed with respect to FIGS. 15A and 15B. In an alternative embodiment, a conical diverter/distributor (FIG. 16) is used for the oxygen-containing feed stream.

The tubular-flow reactor has tubular-flow reactor sleeve 2016 in slideably sealed interface at seal 2008 to housing 2004 and provides a fluid output into a relatively small space defined by housing 2004. Housing 2004 has an axial depth sufficient to accommodate the full axial traverse enabled by threading 2012/2212 (see also FIGS. 22A-22C). Housing 2004 has an output for the reactor product stream at output 2020. Cooling gas input 2002 receives the previously-described cooling gas stream into cooling gas space 2072 (defined between the internal surface of housing 2070 and the external surfaces of sleeve 2016 and blocking tube 2006). The cooling gas stream then proceeds into the internal space of sleeve 2016 via spiral slot 2018, at a point where an axial slot (axial slot 2032 of perpendicular cross section view 2028 across axis 2014 in right-facing orientation at 2042 and of FIG. 23) of blocking tube 2006 and spiral slot 2018 align to define a passageway (2302 of FIG. 23) and also to thereby quenchably cool the internal space of tubular-flow reactor sleeve 2016. Sleeve 2016 therefore co-operates closely with blocking tube 2006.

Sleeve 2016 is sealed to housing 2070 with slideable seal 2074 and thereby rotates to simultaneously process/regress respective to the injectively-mixed backmixing reaction chamber per threads 2012/2212 (FIGS. 22A-22C), regulate the amount of quench delivered to a location within tubular-flow reactor sleeve 2016 (described with FIG. 20 and further described with FIG. 23), and modify the passageway cross-sectional area (fixed-key baffle assembly as previously discussed and further discussed in FIG. 21). While these three degrees of control freedom (baffle positional procession/regression, quench delivery, and baffle passageway cross-sectional area) are therefore not managed with full independence, differences in the rate of change of each with one rotation of sleeve 2016 enables a controllable system having fewer seals than the embodiment described with respect to FIG. 12 and with only very limited convolution between these three degrees of freedom for normal operation. In this regard, one full rotation of sleeve 2016 achieves a full transfer of spiral slot 2018 position (its full axial analog range), perhaps about 2% of the full axial analog range for baffle positional procession/regression, and 600% of the passageway cross-sectional area full axial analog range for a baffle having 6 apertures (FIGS. 17A and 17B). Therefore, sleeve 2016 is first rotated to position within the axial analog range for baffle positional procession/regression, then to position within the axial analog range for quenching, and finally to position within the axial analog range for the passageway cross-sectional area. Insofar as baffle positioning is anticipated to be a relatively strategic operational setting for a particular alkane-gas feed stream composition, real-time operational adjustments should relate more to the single-rotation quench and (⅙ rotation) baffle passageway positioning.

Perpendicular cross section view 2030 across axis 2014 in left-facing orientation at 2040 shows further detail in aperture positioning for inputting feeds from input 2060 and 2062 into the backmixing reaction chamber.

FIG. 21 presents bulkhead/baffle details 2100 for the FIG. 20 reactor system embodiment and also for the alternative embodiment of the interface between the injectively-mixed backmixing reaction chamber and the tubular-flow reactor of the FIG. 12 reactor system embodiment as previously referenced with respect to FIGS. 17A and 17B. Sleeve 2016 is reprised from FIG. 20 with male threading 2012/2212. As described for the alternative embodiment respective to FIGS. 17A and 17B, blocking component 2108 is restrained from rotation by key 2110 (as inserted into slot 1710 (FIG. 17B) and bulkhead 2104 is in non-slideable attachment to sleeve 2016. Ball bearings 2106 interface bulkhead 2104 (end of sleeve 2016) to blocking component 2108. Bulkhead 2104 (sleeve 2016) rotates freely around key 2110 by virtue of non-restraining circular aperture 1714 (FIG. 17A).

As previously discussed, FIGS. 22A-22C show axial positioning details 2200, 2230, and 2260 for the interface between the injectively-mixed backmixing reaction chamber and the tubular-flow reactor of the FIG. 20 reactor system embodiment. Sleeve 2016 is reprised from FIG. 20 with male threading 2012/2212.

Figure 23:
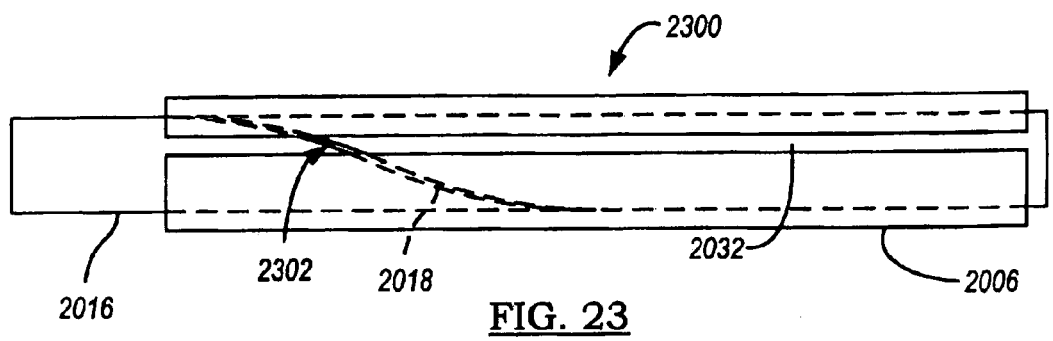
FIG. 23 shows further detail in the quenching inlet for the FIG. 20 reactor system embodiment.

FIG. 23 shows further detail 2300 in the quenching inlet for the FIG. 20 reactor system embodiment. In this regard, a vertical view of sleeve 2016 and blocking tube 2006 in alignment with the axis of entry for input 2002 (FIG. 20) is shown. Sleeve 2016, blocking tube 2006, spiral slot 2018, and axial slot 2032 (view 2028 of FIG. 20) are all reprised from FIG. 20. Location 2302 shows the alignment point of blocking tube 2006 and spiral slot 2018 for delivery of the quenching gas into sleeve 2016 to thereby quenchably cool the internal space of the tubular-flow reactor.

Figure 24A:
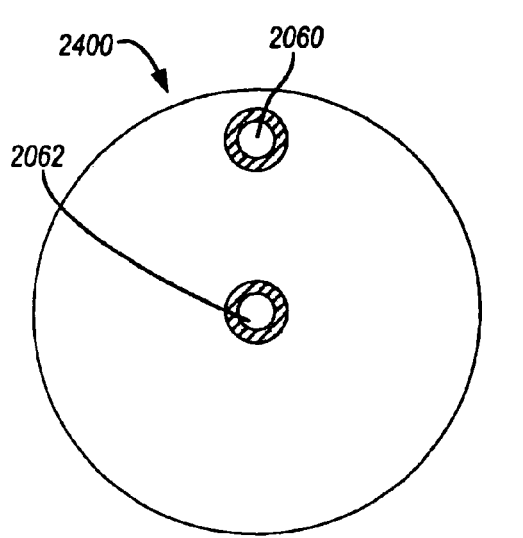
FIGS. 24A and 24B show axial view detail for the FIG. 20 reactor system embodiment.
Figure 24B:
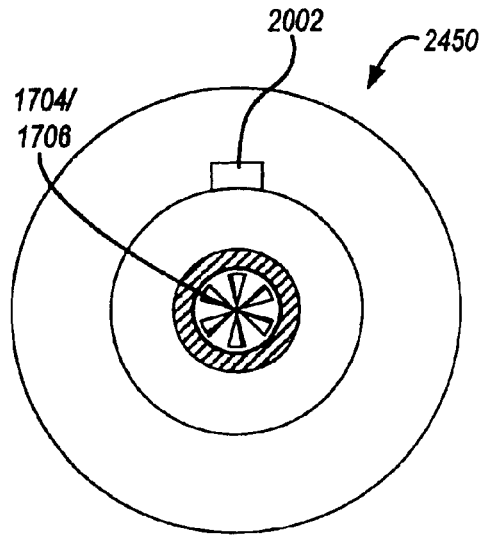

FIGS. 24A and 24B show axial view detail for the FIG. 20 reactor system embodiment. FIG. 24A shows a right-facing view along axis 2014 (FIG. 20) from the outside of the reactor system; inputs 2060 and 2062 are reprised from FIG. 20. FIG. 24B shows perpendicular cross section view 2450 across axis 2014 in left-facing orientation at 2022 (FIG. 20); input 2002 is reprised from FIG. 20 and apertures 1704/1706 are reprised from FIGS. 17A and 17B.

FIGS. 25A and 25B show views 2500 and 2550 of two tubular-flow reactor system embodiments having injectively-mixed entry zones (zone 2520 in both of FIGS. 25A & B), multi-position quenching, and multi-position temperature sensing. Mixing zone 2520 in both FIG. 25A and FIG. 25B shows a symbolic conical distributor diverter 2502 with a full cone, highly similar to the conical diverter of FIG. 16 and also of FIG. 12. System view 2500 of FIG. 25A shows multiple thermocouples (such as thermocouple 2510) and multiple quench inlet ports (such as quench inlet port 2508) in housing 2512. System view 2550 of FIG. 25B shows variable position thermocouple 2504 and a variable position thermocouple quench inlet port 2506 sealing disposed within the internal space defined by housing 2514. Quenching and temperature measurement are therefore highly similar in FIG. 12 and FIG. 25B for the tubular-flow reactors of both of these embodiments. The systems of both FIG. 25A and FIG. 25B are useful in providing reactor systems that are highly similar to the embodiments of FIGS. 12 and 20 except for the absence in FIGS. 25A and 25B of a separating baffle assembly defining a clear interface between an injectively-mixed backmix reaction chamber and the tubular-reactor. In this regard, data from operation of a system of either of FIG. 25A or FIG. 25B, when compared to data from operation of a system of either of FIG. 12 or FIG. 20, has value in indicating efficacy for settings respective to the baffled interface (bulkhead 1232/component 1230 in FIG. 12 or the threaded baffling assembly of FIG. 20).

It will be understood that each of the elements described above, or two or more together, may also find a useful application in other types of methods and constructions differing from the types described above. While the invention has been illustrated and described as embodied in the method of and apparatus for producing methanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method for producing an alkyl oxygenate, the method comprising:
   providing a reactor system comprising an injectively-mixed backmixing reaction chamber comprising a first housing in close coupling to a tubular-flow reactor comprising a second housing, wherein the first housing and the second housing are in slideably-sealed interface;
   feeding an alkane-containing gas feed stream and an oxygen-containing gas feed stream to said injectively-mixed backmixing reaction chamber;
   inducing alkyl free radical formation in said injectively-mixed backmixing reaction chamber to yield an injectively-mixed backmixing reaction chamber product stream comprising oxygen, said alkane, and at least a portion of said alkyl free radicals;
   feeding said injectively-mixed backmixing reaction chamber product stream to said tubular-flow reactor; and
   reacting said injectively-mixed backmixing reaction chamber product stream to produce at least one alkyl oxygenate through partial oxidation of said alkane;
   wherein said alkane is selected from the group consisting of methane, ethane, propane, and butane.

2. The method of claim 1 further comprising modifying the internal volume of the injectively-mixed backmixing reaction chamber from a first internal volume to a second internal volume.

3. A method as set forth in claim 1 wherein feeding of said oxygen-containing feed stream comprises feeding the oxygen-containing stream into a turbulently mixed annular volume from which mixed reacting gases emerge and are conducted axially past an external surface of a converging conical nozzle section of the reactor system toward a tubular flow reactor section, where the induction period is completed.

* * * * *